United States Patent [19]

Parks et al.

[11] Patent Number: 5,073,166
[45] Date of Patent: Dec. 17, 1991

[54] METHOD AND APPARATUS FOR EMPLACEMENT OF A GASTROSTOMY CATHETER

[75] Inventors: Stephen K. Parks; Udi Fishman, both of San Jose; Damon M. Nuckolls, Sunnyvale, all of Calif.

[73] Assignee: Medical Innovations Corporation, Milpitas, Calif.

[21] Appl. No.: 311,685

[22] Filed: Feb. 15, 1989

[51] Int. Cl.$^5$ ............................................. A61M 11/00
[52] U.S. Cl. ....................................... 609/93; 604/105; 604/174; 606/109
[58] Field of Search ................. 604/105–109, 604/93, 174, 78; 606/109; 128/DIG. 26

[56] References Cited

U.S. PATENT DOCUMENTS

| | | | |
|---|---|---|---|
| 1,969,831 | 8/1934 | Williams | 604/178 |
| 3,713,447 | 1/1973 | Adair | 604/105 |
| 4,069,826 | 1/1978 | Sessions et al. | 604/178 |
| 4,393,873 | 7/1983 | Nawash et al. | 604/174 |
| 4,627,838 | 12/1986 | Cross et al. | 604/105 |
| 4,655,752 | 4/1987 | Honkanen et al. | 604/167 |
| 4,666,433 | 5/1987 | Parks | 604/177 |
| 4,685,901 | 8/1987 | Parks . | |
| 4,701,163 | 10/1987 | Parks . | |

OTHER PUBLICATIONS

Miller et al., (1988) Gastrointestinal Endoscopy 34(4):339–342.
Russell et al., (1984) American Journal of Surgery 148:132–137.
Techniques of Percutaneous Gastrostomy, edited by Jeffrey L. Ponsky, M. C., published by Igaku-Shoin, 1988, pp. 1–171.

*Primary Examiner*—Stephen C. Pellegrino
*Assistant Examiner*—Michael Rafa
*Attorney, Agent, or Firm*—Morrison & Foerster

[57] ABSTRACT

A gastrostomy feeding tube including a main, flexible cylindrical body with a proximal end adapted for receiving conventional medical apparatus and a distal end having a locking mechanism. A locking ring is slidably and frictionally attached to the main body of the tube. The locking mechanism includes hinged legs and a membrane surrounding the mechanism, which is attached in a sealed fashion to the tube and to a distal end of the locking mechanism. Other embodiments of the locking mechanism include teeth or detents. Locking knobs are provided within the distal end. A long, rigid insertion tool having grooves for receiving the locking knobs is utilized, and is inserted through a bore through the tube until the locking knobs pass into the grooves. A needle is inserted in a conventional fashion into a patient's stomach, and a guide wire is passed therethrough, and the needle is then removed. The tube and insertion tool are passed over the guide wire, and the insertion tool is then pulled back slightly to pull the hinged legs of the locking mechanism into an expanded configuration, which is maintained by its membrane. The insertion tool is removed, and the tube is held in place by clamping of the patient's skin and stomach between the locking ring and the locking mechanism, respectively. In an alternative embodiment, a locking button is firmly attached to the gastrostomy catheter, and a one-way valve is provided to prevent backflow of gastric juices or the like from the patient's stomach. In both embodiments, a plug is provided for sealing the distal end of the tube.

50 Claims, 9 Drawing Sheets

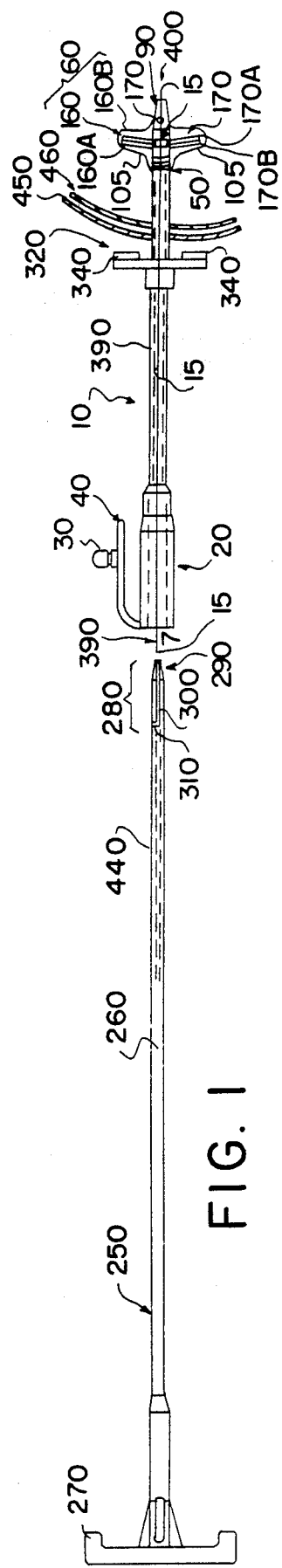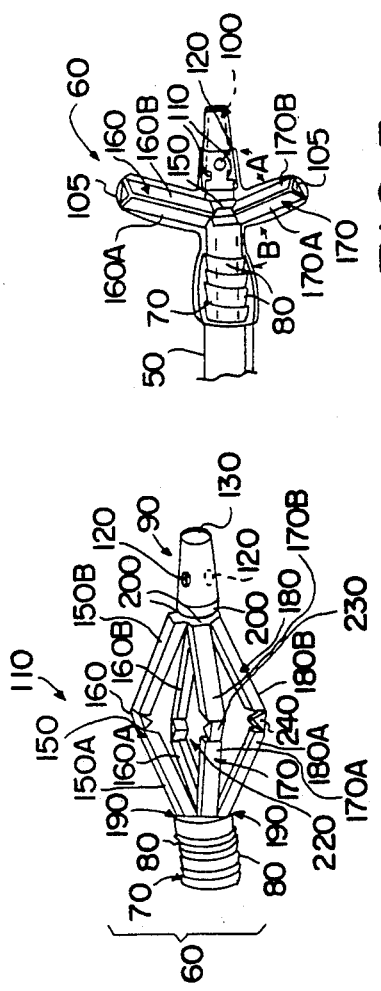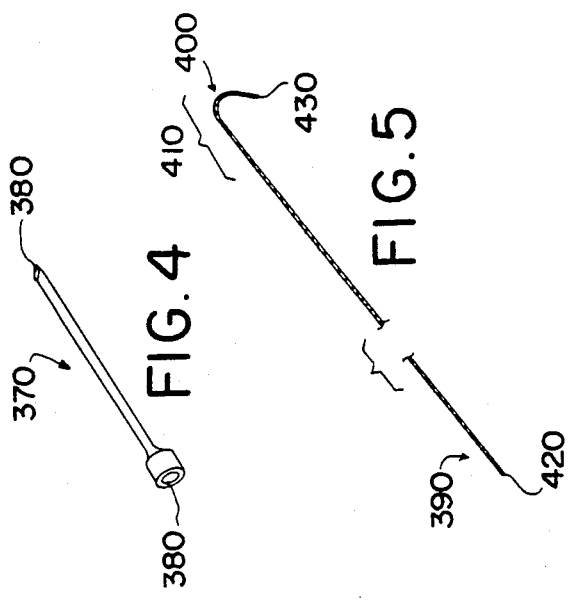

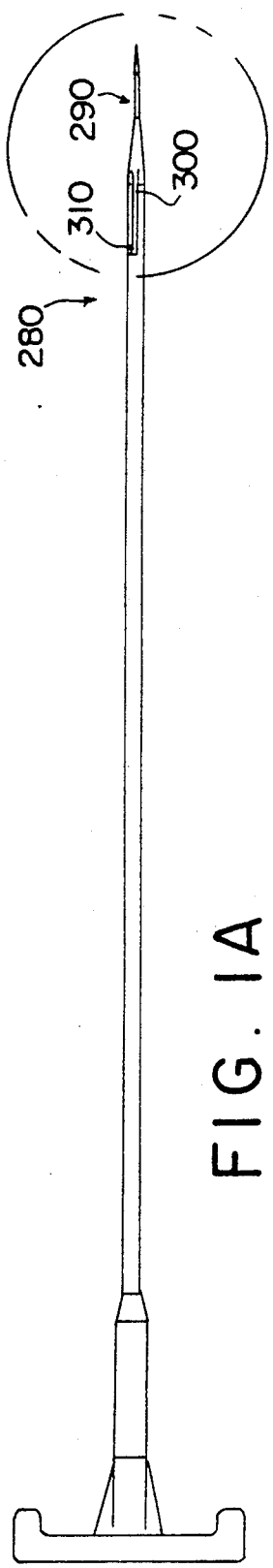
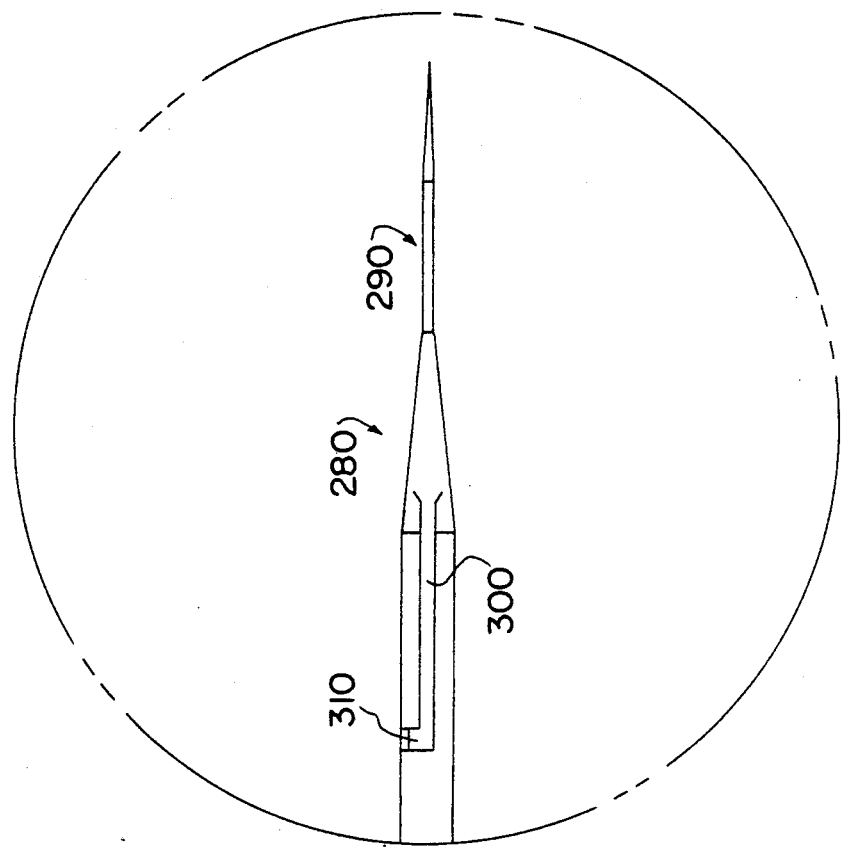

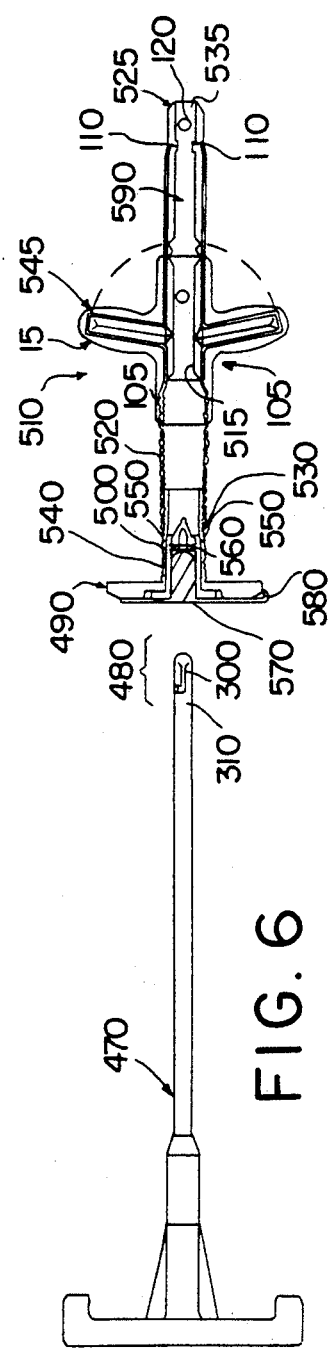
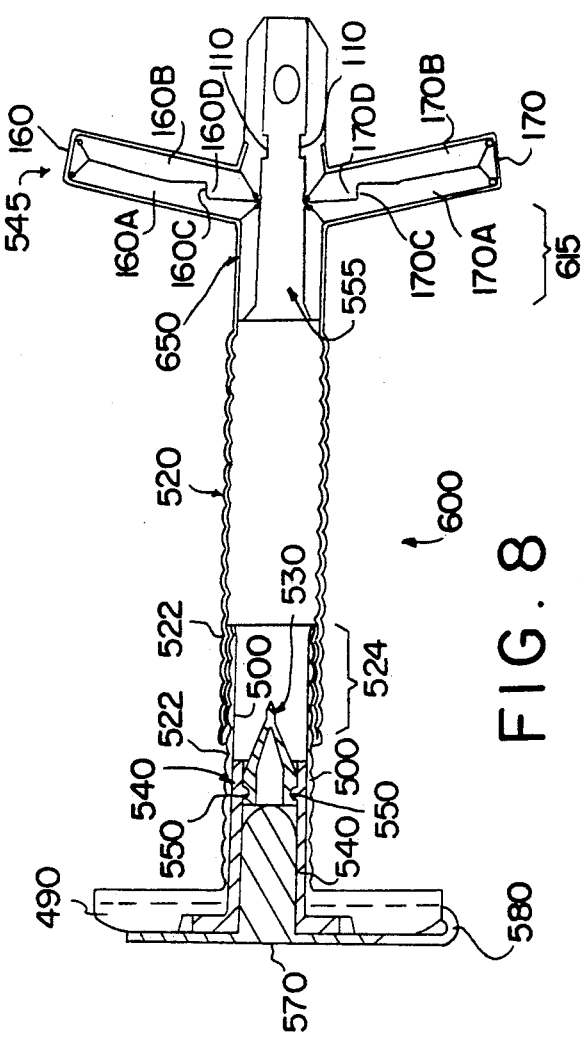
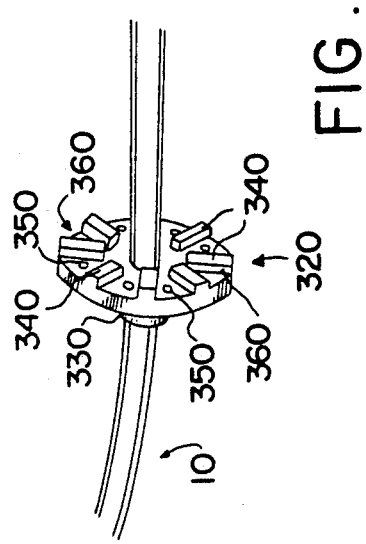

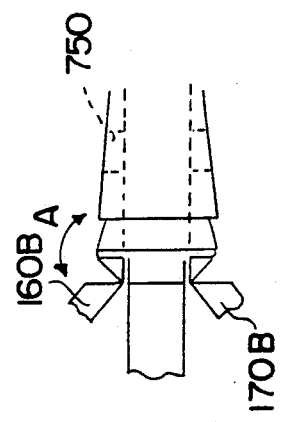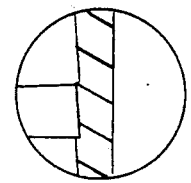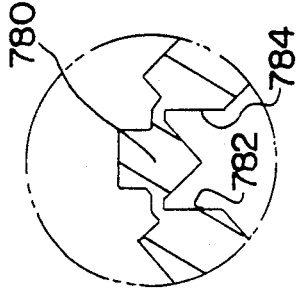

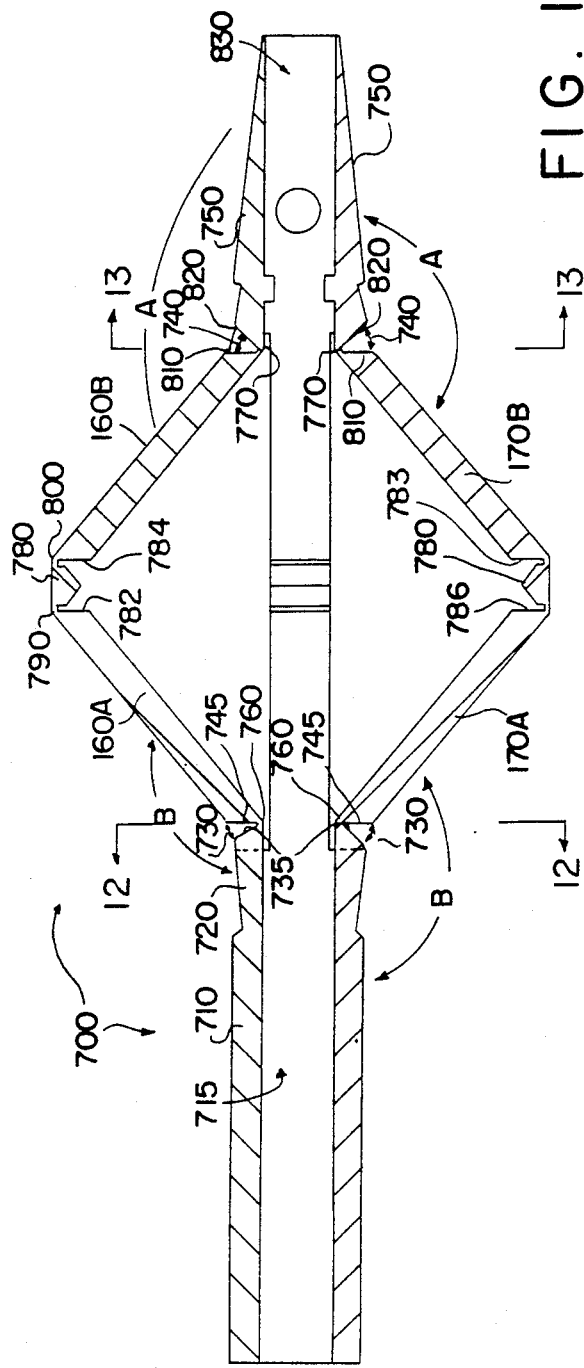
FIG. 11
FIG. 12
FIG. 13
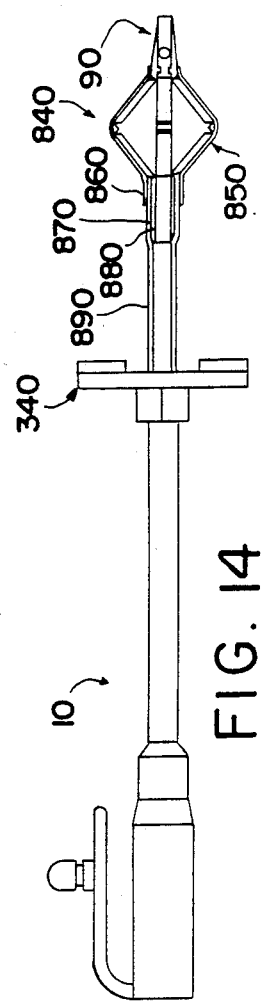
FIG. 14

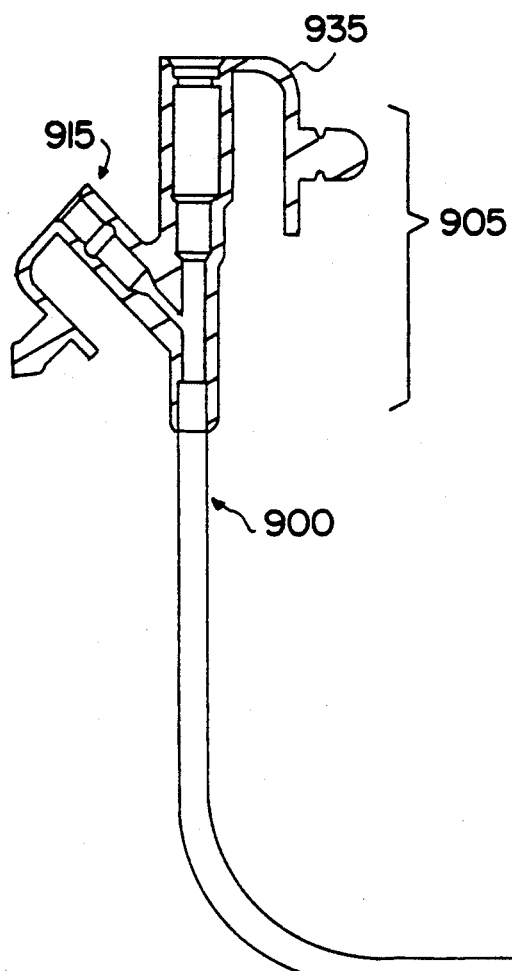
FIG. 15
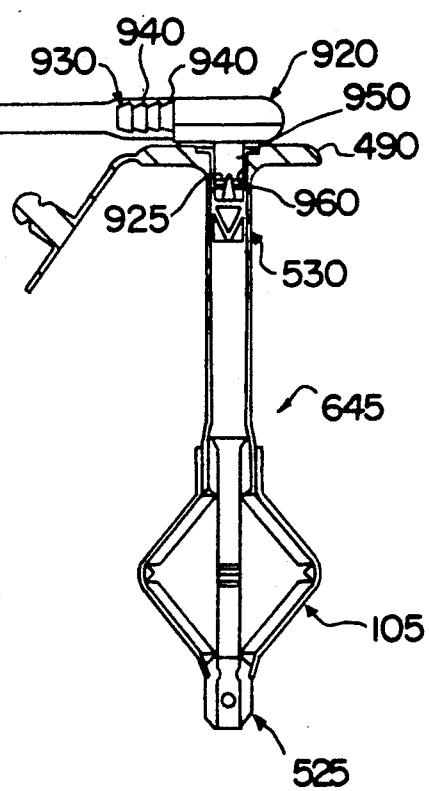
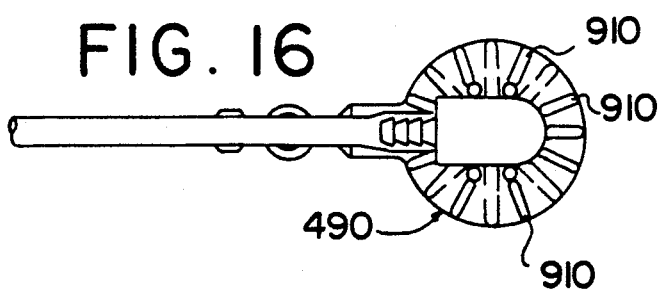
FIG. 16

METHOD AND APPARATUS FOR EMPLACEMENT OF A GASTROSTOMY CATHETER

BACKGROUND OF THE INVENTION

This invention relates to a new gastrostomy feeding tube or catheter and method of insertion. Gastrostomy feedings have been utilized since the late 1800s as a means of providing enteral nutrition to a patient who could not chew or swallow but otherwise had a functional gastro-intestinal system. The gastrostomy catheter allows the delivery of nutrients directly into the stomach of the patient.

Traditionally, these tubes were surgically inserted into the stomach. This required the skill of a surgeon, the use of a sterile operating theater and the presence of supporting staff, i.e., anesthesiologist, nursing team, etc., resulting in substantial cost for the patient. Additionally, the use of general anesthesia provided substantial risk to the compromised patient. Recently, the percutaneous endoscopic gastrostomy (PEG) was developed. This procedure could be performed outside the operating room, under local anesthetic and by a gastro-enterologist, thereby eliminating much of the cost and risk of general anesthesia.

The PEG procedure can be divided into two types of procedures, the "push" (or "stick") procedure and the "pull" procedure. This invention relates to the development of a new gastrostomy catheter designed as a new type of "push" procedure.

In a conventional "pull" procedure, an endoscope is inserted through the esophagus of the patient, and the stomach is then inflated. Using the endoscope to locate an appropriate site in the stomach wall, a cannula or needle is then inserted through the stomach wall, and a string is inserted through the needle. The needle may then be removed. The string is grasped by means of a snare passing through the endoscope, and the endoscope and snare are pulled up through the esophagus, such that one end of the string comes out through the mouth, leaving the other end protruding through the opening made by the needle. A gastrostomy catheter is then tied to the end of the string which protrudes from the mouth, conventionally by means of another string attached at one end of the gastrostomy catheter.

The catheter is then pulled down into the stomach, by pulling on the end of the string which protrudes through the opening in the stomach, and is pulled through the opening as well, usually being provided with a tapered dilator at the leading end to assist in passing through the stomach wall. The catheter is held in place by a retention means against the interior of the abdominal wall. Another retention means is placed on the exterior, so as to hold the catheter in place against the stomach. The endoscope is reinserted to ensure proper placement of the catheter.

The pull procedure has several disadvantages, one of which is the fact that, for both emplacement and removal, an endoscope must be inserted into the patient's esophagus, requiring anesthesia and causing discomfort to the patient. Also, the catheter itself must pass through the patient's esophagus, once for emplacement and once for removal. This becomes even more problematic when secondary or replacement catheters are put in place, since each time the catheter is changed, the "pull" procedure must again be followed, with increased likelihood of trauma, infections, and other complications.

The pull procedure is particularly difficult to carry out when a patient has an obstruction in the esophagus, which is a problem compounded by the fact that it is just such people who are likely to need the procedure. Another disadvantage arises from the fact that infectious or cancerous matter may be drawn from a diseased area in, for example, the throat, down into the stomach, with the possibility of spreading the disease further, especially to the area around the freshly formed opening in the stomach.

Accordingly, a need has arisen for a gastrostomy catheter and method for emplacement which does not require access to the stomach via the esophagus.

Percutaneous gastrostomy techniques are described in detail in articles by R. Miller, et al., "The Russell percutaneous endoscopic gastrostomy: key technical steps," Gastrointestinal Endoscopy 1988: 34; 339-342, and T. Russell, et al., "Percutaneous Gastrostomy—A New Simplified and Cost-Effective Technique," American Journal of Surgery 1984:148; 132-137, which are incorporated herein by reference.

In the technique set forth by Russell, sometimes referred to as the "push" technique, a needle is first inserted into the stomach (at a site located by endoscopy, as with the pull procedure), and then a guide wire is inserted through a lumen in the needle. A small incision is then made in the fascia next to the guide wire, after which an interiorly lubricated sheath having a splittable seam is guided, along with a tapered dilator, over the guide wire and into the stomach. Once the sheath is in place, the dilator and guide wire are removed, and a balloon catheter is inserted through the lubricated central lumen of the sheath. A distal balloon of the catheter is then inflated, and the sheath is peeled or split away along its seam or seams, thus leaving the catheter emplaced in the stomach. Sutures are provided to maintain tension of the balloon against the peritoneum.

A disadvantage of the Russell procedure is that the splittable sheath is necessarily larger in diameter than the catheter which is inserted through it for emplacement within the stomach. Therefore, the opening into the stomach is made overly large, making sealing difficult and increasing the likelihood of infection. The sheath may not be made too narrow, or the physician will not be able to insert the catheter through it, and thus there is a trade-off between insertability of the catheter and the quality of the seal once the catheter is in place.

Another disadvantage of the Russell procedure is that the balloon is necessarily soft and flexible, because it must be capable of being inflated and deflated, and of being passed through the small opening into the stomach in its deflated state. Therefore, the balloon does not provide a very firm anchor for the catheter; and this is a disadvantage to all techniques relying upon balloons as anchors.

Another disadvantage of the Russell technique is that it requires the use of the splittable sheath, which increases the expense of the emplacement of the catheter.

After a gastrostomy catheter is in place, it is desirable to replace it after a time with a secondary, or replacement catheter. Such catheters are available, and a typical replacement catheter uses a flexible, enlarged tip attached at the distal end of the catheter. To insert this into the patient, a rigid rod is inserted through a lumen of the catheter into the enlarged tip, and is pressed against the inside of the tip, thus stretching it out and decreasing its diameter. In this configuration, the tip is then inserted through the opening into the stomach, and the rod is removed, allowing the tip once again to enlarge, thus providing an anchor against removal of the catheter.

This type of catheter does not provide a very reliable anchor, however, because the flexible tip may be stretched into a reduced-diameter configuration simply by a pull on the portion of the catheter which is exterior to the opening. Thus, there is always the concern that an accidental force on the catheter will result in its removal, perhaps with consequent damage to the area surrounding the opening and bleeding of the patient.

Another disadvantage of this design is that there is a direct trade-off between the expanded and reduced diameters, respectively, of the flexible tip. A larger expanded diameter leads to a more reliable anchor, and is especially necessary in a flexible-tip design. However, a larger expanded diameter requires a greater amount of material in the tip, and thus when the rod is used to stretch the tip out longitudinally, in order to reduce its diameter for insertion, this greater amount of material limits the minimum diameter, such that the tip, even when in its reduced state, may have a diameter appreciably larger than the diameter of the catheter. This leads to undesirable enlargement of the opening into the patient, resulting in less reliable sealing around the catheter once it is in place, and in greater likelihood of infection at the insertion site.

Replacement catheters often have a shorter length than primary catheters, and thus there is the problem of possible fluid leakage from the stomach through the catheter. This is not so much a problem with a longer catheter, because back-pressure is developed by the fluid. Thus, with a shorter catheter, it is helpful to provide a valve somewhere along the catheter.

One such valve is a check valve comprising a flap positioned adjacent the enlarged tip, designed to prevent backflow of fluids up the catheter, but to allow flow of fluids into the stomach. A problem with this design is that the flap may get caught in the portion of the catheter directly proximal its attachment point, thus maintaining the valve in permanently open state and defeating the check valve. Another problem with this design is that compression on the area around the valve, such as due to stress on the stomach, may force the flap open, allowing fluids to back up out of the catheter. A further problem is that, in order to decompress the patient's stomach, the valve must be opened by a rigid tool inserted into the patient's stomach.

Another type of valve used with replacement catheters is screwed to the proximal end of the catheter. This has the disadvantage of being bulky and relatively expensive, and of requiring at least a two-part system.

SUMMARY OF THE INVENTION

It is an object of this invention to provide a new PEG catheter which eliminates the use of the dilator and splittable sheath such that the tube is passed over the guide wire as above and into the stomach. The internal retention mechanism, a mechanically operated "mushroom" locking mechanism, is activated. Tension is placed on the catheter to position the stomach against the abdominal wall.

It is another object of this invention to provide a new PEG catheter with an internal retention mechanism which secures the stomach to the abdominal wall more securely and reliably than the current balloon or mushroom catheters.

It is yet another object of the invention to provide such a tube or catheter which is suitable for use in peritoneal dialysis, urological applications, and other medical purposes.

It is a further object of the invention to provide a non-surgical means of inserting a catheter into the internal organs without the need either for a dilator device or for a removable needle, which are devices currently used to facilitate the insertion of catheters or other instruments into the body, and are removed after insertion and discarded.

It is yet another object of this invention to provide a catheter having a distally carried anchor which is collapsible and expandable, wherein the collapsed configuration has a diameter which matches the diameter of the catheter, and wherein the diameter of the anchor in the collapsed configuration is independent of the diameter in the expanded configuration.

This invention provides a simplified method of inserting all types of hollow and flexible catheters without the need for a dilator or an introducer sleeve.

Another object of this invention is to provide a permanent and secure method of fixing the catheter to the internal organ of the patient without the use of a balloon, a fixed ring, large plugs, or the like.

It is further object of the invention to provide a method and apparatus for emplacement of a catheter by a push procedure, wherein the opening into the patient is not enlarged beyond the diameter of the catheter.

It is another object of the invention to provide such a method and apparatus wherein a reliable valve is provided which is exterior to the patient when the catheter is in place, and which allows emplacement and removal of the catheter without removal of the valve.

It is a particular object of the invention to provide such a method and apparatus for emplacement of a catheter wherein the catheter may be repeatedly inserted and removed, if necessary.

It is a further object of the invention to provide such a method and apparatus wherein endoscopy is unnecessary for emplacement of the catheter.

The invention comprises a method and apparatus for emplacement of a gastrostomy catheter within a stomach. A gastrostomy catheter of the invention for primary emplacement includes a proximal end, a main body, and a distal end, with a locking mechanism attached at the distal end. The locking mechanism includes a first end, a second end, and a plurality of hinged legs carried therebetween. The locking mechanism has a fully extended configuration and a retracted configuration. In the fully extended configuration, the outer diameter of the locking mechanism closely matches the outer diameter of the gastrostomy catheter. In the retracted configuration, branches of each of the hinged legs are pulled back until they meet one another, until a T-shaped cross section is achieved, and the outer diameter of the T-shape is much greater than the outer diameter of the gastrostomy catheter.

The distal end of the locking mechanism includes an inner bore and two locking knobs, and in addition includes both lateral and terminal ports. The proximal end of the gastrostomy catheter is configured for receiving conventional medical apparatus for providing nutrients, medications, or the like into the stomach of the patient. A plug is provided for closing off the lumen of the gastrostomy catheter.

A flexible, elastic membrane is provided over the locking mechanism, and seals with the gastrostomy catheter and distal end of the locking mechanism. A continuous fluid passage is thus formed by the lumen of the gastrostomy catheter, the interior of the membrane, and the interior bore of the distal end of the locking mechanism.

An insertion tool is used, which is preferably a long rigid rod with a handle and a plurality of longitudinal grooves at its distal end, each groove having a right-angled portion set back from the distal end. The insertion tool is inserted through the bore of the gastrostomy catheter until the longitudinal grooves receive the locking knobs of the distal end of the locking mechanism, and the insertion tool is then rotated such that the locking knobs enter the right-angled portions, thus locking the distal end of the insertion tool and the gastrostomy catheter with respect to longitudinal motion.

For insertion of the primary insertion embodiment of the gastrostomy catheter of the invention, a conventional needle is first inserted into the stomach of a patient, at a site located by endoscopy, and a flexible guide wire is inserted through a lumen in the needle. The needle is then removed, and the insertion tool and gastrostomy catheter (locked together as described above) are inserted over the guide wire, slightly enlarging the opening originally made by the needle. The gastrostomy catheter is somewhat flexible, such that it will fit tightly into this opening, and the insertion tool provides rigidity so that the catheter may be inserted through the opening. The locking mechanism of the primary insertion catheter is gradually tapered at its distal end, and the distal end of the locking mechanism is also gradually tapered and closely matches the diameter of the distal end of the locking mechanism, so as to minimize the enlargement of the opening into the stomach. This minimizes trauma to the patient, and provides a good seal against the passage of fluids or infectious material.

A retaining ring or button is slidably attached to the exterior of the gastrostomy catheter, and is slid against the skin of the stomach of the patient. The operator of the device pulls back on the insertion tool, until the locking mechanism is in its expanded configuration. The insertion tool is then removed, by first rotating it so as to disengage it from the locking mechanism, and then pulling it axially outwards.

The expanded configuration of the locking mechanism is maintained by the tension of the membrane, which is elastic and contracts against the locking mechanism. The locking mechanism is biased slightly from the orthogonal when in the expanded configuration, such that the membrane, exerting an axially inward force on the mechanism, maintains it tightly in its expanded configuration. Thus, the gastrostomy catheter is maintained tightly in place by the retaining ring on the exterior of the patient's stomach and the locking mechanism on the interior thereof.

Thus, the catheter tip of the invention can be introduced into the internal organs of the body, such as the gastric cavity, and then locked into place with the insertion tool. This provides permanent placement, secure against being accidentally dislodged by an unintentional pull, but permits easy removal with the appropriate tool.

In an alternative embodiment, involving a secondary feeding catheter, the retaining ring may be unitary with or firmly attached to the gastrostomy catheter. In this embodiment, which is for use as replacement catheter after removal of the primary catheter, the distal end of the locking mechanism may be rounded, and the proximal end of the catheter is shorter, and includes an adaptor for accommodating conventional apparatus for supplying medicines, nutrients, or the like. A one-way flexible valve is preferably provided within the bore of the gastrostomy catheter to prevent backflow of gastric juices, medications, or the like.

An alternative embodiment to the locking mechanism includes detents on the branches of the mechanism, which interlock when the mechanism is expanded, thus maintaining the mechanism in the expanded configuration. In this embodiment, there is no need for the membrane described above relative to the earlier embodiments.

In a preferred embodiment, the legs of the locking mechanism are biased forward by means of angles recesses situated in the body of the catheter, which are configured to closely match surfaces of the branches, such that, upon expansion of the mechanism, a predetermined angle is achieved by the mechanism.

In one embodiment, the locking mechanism and a main shaft of the catheter are held together by the engagement of teeth or threads attached to each, such that the effective length of the catheter may be altered. This allows for versatility in accommodating different widths of abdominal walls, such that one design of catheter may be used for many different patients.

Another embodiment of the invention includes a locking mechanism with interior, axially disposed teeth carried on the distal end of the mechanism, which interlock with teeth carried on a collar attached to the branches of the mechanism. In this embodiment, the teeth interlock with one another when the physician pulls back on the insertion tool, thus expanding the mechanism. The teeth are allowed to disengage when the insertion tool is pulled yet further back, and the mechanism then collapses into a nonexpanded configuration, for removal of the catheter from the patient.

A removal tool is provided for disengaging certain of the foregoing embodiments of the catheter of the invention, the tool having a shaft which is rectangular in cross section, such that when it is inserted into a central bore of the catheter, it engages the locking knobs carried in the distal end of the locking mechanism. The tool is then pushed forward, thereby disengaging the locking mechanism, which collapses into its nonexpanded configuration for removal from the patient. The rectangular shape of the shaft is such that it preferably cannot be received into a bore of the distal end of the locking mechanism, such that the tool can be used only for removal, and not for insertion, of catheters of the invention.

BRIEF DESCRIPTION OF THE DRAWINGS

FIG. 1 shows a catheter and insertion tool according to the invention.

FIG. 1A shows an alternative embodiment of the insertion tool shown in FIG. 1.

FIG. 1B is an enlarged view of a portion of FIG. 1A.

FIG. 2 shows a locking mechanism of the invention in a partially extended configuration.

FIG. 3 shows the locking mechanism of FIG. 2 in a fully expanded configuration.

FIG. 4 shows a needle for use with the invention.

FIG. 5 shows a guide wire for use with the invention.

FIG. 6 shows an alternative embodiment to the apparatus of FIG. 1.

FIG. 7 shows a retaining ring for use with the invention.

FIG. 8 shows an alternative embodiment of the apparatus of FIG. 6, showing a detent mechanism.

FIG. 11 is a detailed drawing, with dimensions in inches and angles in degrees, of a preferred embodiment of the invention.

FIG. 11A is a view like that of FIG. 11 of another embodiment of the invention.

FIGS. 11B and 11C are close-up views of the areas designated in FIG. 11A by arcs 11B and 11C, respectively.

FIG. 11D is a close-up view of the forward portion of the device shown in FIG. 11A.

FIG. 12 is a sectional drawing taken along line 12—12 of FIG. 11.

FIG. 13 is a sectional drawing taken along line 13—13 of FIG. 11.

FIG. 14 shows an alternative embodiment to the apparatus of FIG. 1.

FIG. 15 shows the apparatus of FIG. 10 in use with a feeding catheter.

FIG. 16 is a top view of a portion of the apparatus of FIG. 15.

FIGS. 17-22 show various views and configurations of an alternative embodiment to the locking mechanism of the invention.

DETAILED DESCRIPTION OF THE PREFERRED EMBODIMENTS

Figure 9:
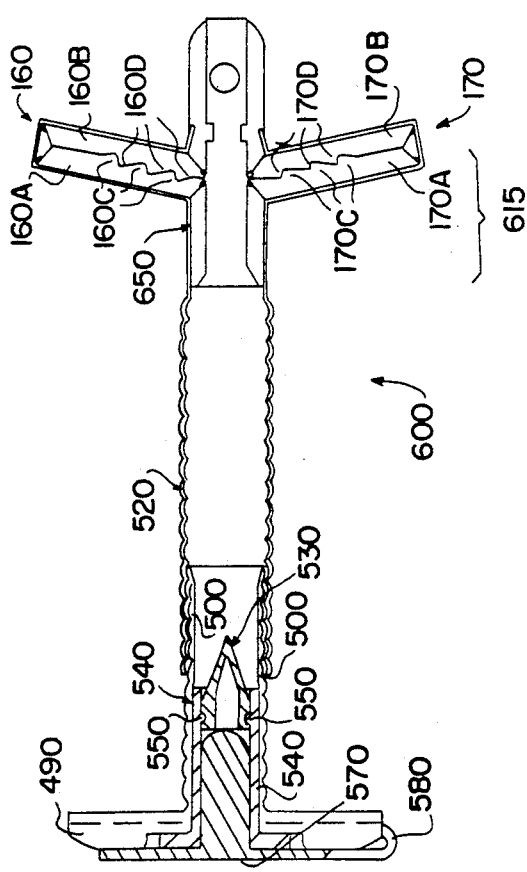
FIG. 9 shows another alternative embodiment to the apparatus of FIG. 6, showing another detent mechanism.

FIG. 1 shows a gastrostomy feeding catheter 10 according to the invention, which is preferably of a hypoallergenic, biocompatible, flexible substance such as silicon. The catheter 10 includes a proximal end 20 which is adapted for receiving medical apparatus in a conventional manner. A plug 30 is carried on a flap 40, which is attached in a flexible or hinged fashion to the proximal end 20. The plug 30 is adapted to fit snugly into a central bore 15 of the proximal end 20.

The catheter 10 also includes a distal end 50, and a locking mechanism or anchor 60 is attached, as shown in FIGS. 1-3. The mechanism 60 is preferably formed of a rigid, biocompatible material such as polypropylene or the like. The mechanism 60 is generally cylindrical in configuration, and includes a first end 70 which is provided with annular ridges or teeth 80, which are angled to the right from the point of view of FIGS. 1-3. The distal end 50 of the catheter 10 has an inner diameter which closely conforms to the outer diameter of the first end 70. The distal end 50 may be fused, glued, or otherwise joined to the first end 70. One manner of joining these is to fit the distal end 50 tightly over the first end 70, as shown in FIG. 3, slightly distending the end 50 in doing so. The elasticity of the material from which the catheter 10 is formed causes the end 50 to contract tightly against the ridges 80, thus forming a reliable connection between the catheter 10 and the mechanism 60.

The mechanism 60 also includes a second end 90, which is generally frustoconical or tapered in shape, and includes a bore 100. Disposed within the bore 100 is at least one, but preferably two, locking knobs 110, with a function to be described below. The second end 90 is provided with lateral ports 120 and a terminal port 130, which are exit ports for fluid introduced into the catheter 10.

The mechanism 60 also includes a central portion 140 comprising legs 150, 160, 170 and 180. The first end 70, the second end 90, and the central portion 140 are preferably formed in a unitary fashion.

In the preferred embodiment, there are four legs 150-180, as shown in FIG. 2, but other numbers of legs may be utilized. Each leg, such as leg 150, is attached in a hinged fashion at hinges 190 to the first end 70, and is also attached in a hinged fashion at hinges 200 to the second end 90. Each leg is also hinged in the middle, forming two branches for each leg, namely, branches 150A-B, 160A-B, 170A-B, and 180A-B. The branches 150A and 150B are hinged together at a hinge 210, and likewise the branches of each of the legs 160, 170 and 180 are hinged at hinges 220, 230, and 240, respectively.

Thus, the locking mechanism 60 may be configured to be fully extended, such that the branches 150A, 160A, 170A and 180A are substantially collinear with the branches 150B, 160B, 170B and 180B, and are substantially parallel to one another. FIG. 2 shows a partially extended configuration, whereas FIGS. 1 and 3 show a completely expanded position, wherein branches 150A, 160A, 170A and 180A are substantially parallel to and adjacent the branches 150B, 160B, 170B and 180B, respectively. As discussed in detail below relative to FIG. 11, the legs 150-180 are configured such that they are angled forwardly when the mechanism 60 is in its expanded configuration.

A flexible, somewhat elastic membrane 105 is fitted over the locking mechanism 60, and overlaps the distal end 50 in the region of the ridges 80, as shown in FIGS. 1 and 3. The membrane 105 covers the legs 150-180, and also is tightly configured to match the outer diameter of the second end 90 of the locking mechanism 60.

The membrane 105 forms a fluid-tight seal with the catheter 10 and the end 90. Fluid passing through the bore 15, shown in FIG. 1, also passes the locking mechanism 60 and out through the ports 100 and 120 without any leakage between the membrane 105 and the catheter 10 or between the membrane 105 and the second end 90, thus forming a continuous fluid channel in the interior of the catheter 10 and the membrane 105 between the proximal end 20 and the second end 90.

The elasticity and flexibility of the membrane 105 are selected such that when the mechanism 60 is in the configuration shown in FIGS. 1 and 3, the membrane 105 contracts tightly against the mechanism 160. The mechanism 60 may be repeatedly drawn into the configuration shown in FIGS. 2 and 3, respectively, by pulling or pushing on the first end 70 with respect to the second end 90, and each configuration is maintained until affirmative force is applied towards the other configuration The branches 150A-180A are in the preferred embodiment slightly longer than the branches 150B-180B, and the branches are configured (as discussed in detail relative to FIG. 11 below) such that, when the locking mechanism 60 is in the expanded configuration, the branches will lie at somewhat less than a right angle to the catheter 10, as shown in FIG. 1. The mechanism 60 is maintained in this configuration by the axially inward force exerted by the membrane 105 between the legs 150-180 and the distal end 50 of the catheter 10.

It will be appreciated that both the expanded and collapsed (or collinear, extended) configurations of the mechanism 60 are resting configurations. That is, there is no tool or force necessary to maintain these configurations; rather, they are stable configurations. This is unlike the apparatus and methods of conventional design, wherein distal end buttons have partially collapsed configurations, but only when a force is affirmatively applied thereto.

FIG. 11 shows a detailed drawing of a locking mechanism 700 which is an alternative to the embodiment of the locking mechanism 60 of FIG. 1, wherein the structure of the branches 150-180 is identical, but with slightly altered features in the collar of the mechanism. FIGS. 11A-11D show detailed drawings of a locking mechanism, also referred to by the numeral 700, which is substantially identical to the mechanism 60. In the following discussion, reference to FIG. 11 should be understood also to apply to FIGS. 11A-11D, although, as seen from an inspection of these figures, there are certain structural and design differences.

The features of the mechanism 700 may be incorporated into any of the embodiments herein. In FIG. 11, linear dimensions are expressed in inches, and angular dimensions are expressed in degrees. As with the various embodiments described above, identical numerals will refer to identical or substantially identical features of other embodiments of the invention.

The mechanism 700 shown in FIG. 11 includes a shaft 710 and a collar 720. The mechanism 700 includes four legs 150-180, as in the above-discussed embodiments, although only legs 160 and 170 are shown in FIG. 11.

Each of the branches 150A-180A is attached to the collar 720 and forms an angle 730 with respect thereto. When the mechanism 700 is in the position shown in FIG. 11, this angle 730 is approximately 42 degrees. However, when the branches 150A-180A lie collinear with the branches 150B-180B, this angle is preferably approximately 82 degrees. Thus, there is an approximately 82-degree range of movement for the branches 150A-180A with respect to the collar 720. At the maximum expansion of the branches 150A-180A (as in FIG. 3), when the surfaces 735 and 745 forming the angles 730 abut one another, the angle B (between the branches 150A-180A and the axis of the collar 720) is 100 degrees.

Similarly, an angle 740 is formed between each of the branches 150B-180B by the surfaces 810 at the forward ends of the branches 150B-180B and the surfaces 820 formed on the forward end 750. In this embodiment, angle 740 is 100 degrees (which is the supplement of the angle 730) when the mechanism 700 is in its flat configuration, i.e. when the branches 150A-180A and the branches 150B-180B are substantially collinear to one another. Thus, angle 740 is such that branches 150B-180B lean forwardly when the mechanism 700 is in its fully expanded configuration (as in FIG. 3), resulting, in this embodiment, in an 80 degree angle for angle A between the branches 150B-180B and a central axis 830 of the shaft 710.

Other angles 730 and 740 are usable, such as 82 degrees and 98 degrees, respectively, or other combinations of angles which result in a sufficient angle for the branches 150-180 when the locking mechanism is in its expanded configuration such that the mechanism will be held in place by the axially inward force of the surrounding membrane. In general, when the legs are in their collinear configuration, angle 730 should be less than 90 degrees and angle 740 should be greater than 90 degrees; and when the mechanism 700 is in its expanded configuration, angle A should be less than 90 degrees, while angle B should be greater than 90 degrees. In general, the sum of angles A and B will be 180 degrees Branches 150A-180A are joined to the collar 720 by means of interior hinges 760, and branches 150B-180B are joined to the forward end 750 by interior hinges 770. The hinges 760 and 770 may be plastic membranes formed in a unitary fashion with the collar 720 and the branches 150A-180A, and with the branches 150B-180B and the forward end 750, respectively.

A stop 780 is disposed between each pair of branches 150A-150B, 160A-160B, 170A-170B, and 180A-180B. Each stop 780 is joined to the adjacent branches by exterior hinge membranes 790 and 800, and may be formed in a unitary fashion with the respective branches. The stop 780 is preferably triangular in shape, and abuts against the ends 782, 784, 786 and 788 of the branches 160A, 160B, 170A and 170B, respectively. The angles of the edges of the stop 780 and of the ends 782-788 are such that, when the mechanism 700 (or 60) is in the configuration of FIG. 3, each pair of branches is in a parallel configuration; but the branches are prevented from sliding against one another by the stop 780, which exerts a binding force against each of the branches. In addition, any force on the mechanism 700 from, for example, the stomach wall, is distributed by the stop 780 to the branches, and is further transmitted by the branches to the surface 820. Thus, the predetermined combination of angles results in such external forces actually causing the mechanism to seat even more tightly in its expanded configuration. The distribution of forces lowers the likelihood that a force at any particular point will cause failure or collapse of the mechanism.

An insertion tool 250 (shown in FIG. 1) is utilized with the invention, comprising a long, rigid, preferably metal rod 260, a handle 270, and a tip 280. The tip 280 includes a frustoconical or tapered section 290, which is adapted in size and shape to closely match the shape of the bore 100 of the second end 90 of the locking mechanism 60. A groove 300 runs parallel to the length of the tip 280 and extends to the end of the section 290, and includes an angled portion 310, which is preferably at substantially a right angle to the length of the tip 280, as shown in FIG. 1. Other angles than a right angle may be used for the portion 300, including acute angles. Another groove (not separately shown) is provided symmetrically opposite to the groove 300, and also includes an angled portion, such as angled portion 310.

Referring now to FIG. 11, when the insertion tool 250 is utilized to pull back on the forward end 750, the disposition of the hinges 760, 770, 790 and 800, coupled with the presence of the insertion tool within the bore 715 of the shaft 710, ensures that the branches 150A-180A and 150B-180B can move only outwards. As a result of the radial offset of the interior hinges 760 and 770 and the exterior hinges 790 and 800, the branches 150A-180A and 150B-180B buckle outwardly; if it were not for the radial offset of the hinges, the branches might jam up against one another, without moving outwardly. Because of the tool 250 being within the mechanism 60, there is no chance that the branches will buckle inwardly against one another.

When the insertion tool 250 is moved all the way back, the branches take on their forwardly-angled configuration of FIG. 3, and the stops 780 prevent the branches 150A–180A from moving further relative to the branches 150B–180B. As discussed above relative to the embodiment of FIGS. 1–3, a force is exerted by the membrane 105 in an inwardly axial direction against the legs 150–180, which keeps the mechanism 700 (or the mechanisms 60) in the expanded configuration, and provides high stability which is enhanced further by any pressure of the stomach wall against the branches 150A–180A.

The outer diameter of the mechanism 60, whether in its expanded or collapsed configuration, is independent of the number of branches or legs which it includes, and the expanded diameter is independent of the collapsed diameter.

A retaining button or locking ring 320 is configured to fit in a tight, frictional manner over the catheter 10. The locking ring 320 includes a collar 330, a plurality of raised, radially disposed ridges 340, air vents 350 alternating with the ridges 340, and air gaps 360 formed between the ridges 340. The locking ring 320 is utilized in a manner described below, and as further described in U.S. Pat. No. 4,666,433, which is incorporated herein by reference.

The device as shown in FIGS. 1–3 and 7 is utilized in the following manner. First, a needle 370 having a lumen 380 (see FIG. 4) is inserted through the skin and into the stomach. A guide wire 390 (shown in FIG. 5) is then inserted through the lumen 380. The guide wire 390 includes a bight 400 at its distal end 410, and is preferably formed of a tightly coiled metal, brazed at its distal tip 430, to maintain the coiled configuration. Brazing may also be used to maintain the shape of the bight 400. Other means of maintaining the coiled configuration and the bight shape may be used, including adhesives, welds, or the like. The bight 400 is flexible, as is the entire guide wire 390, such that it may be straightened out to be inserted through the lumen 380 and into the stomach. Once the distal end 410 of the guide wire 390 passes out of the tip of the lumen 380 and into the stomach, it returns to its bight-shaped configuration.

Once the guide wire is in place, the needle 370 may be removed. The insertion tool 250 is inserted through the bore 15 of the catheter 10, such that its tip 280 passes through the bore 100 of the locking mechanism second end 90. When the tip 280 passes into the bore 100, resistance is met thereto by the knobs 110 within the bore 100, and the insertion tool 250 is rotated until the grooves 300 align with the knobs 110, at which point the tip 280 may pass further into the bore 100, until the knobs 110 contact the right-angled portions 310. The insertion tool 250 is then rotated (clockwise as viewed from left to right in FIG. 1), such that the knobs 110 are within the portions 310, and prevent further longitudinal movement of the insertion tool 250 relative to the locking mechanism 60. The insertion tool and gastrostomy catheter 10 are then slid in tandem over the guide wire 390, a bore 440 (shown in part in FIG. 1) being provided through the center of the insertion tool 250 to accommodate the guide wire 390. The catheter 10 is thereby inserted through the opening originally formed by the needle 370 and into the patient's stomach (or other area under treatment), with the rigidity of the tool 250 supporting the catheter during insertion, allowing it to be pushed through the opening made by the needle 370.

The conical shapes of the tip 280 and of the end 90 allow the insertion tool 250 and the catheter 10 to pass into the opening to the patient's stomach with minimal enlargement thereof, ensuring a tight fit for the catheter 10. This is further ensured by configuring the very end of the tip 280 outer diameter closely matches the diameter of the second end 90 at the point of contact, so that there is an essentially continuous and gradual increase in the diameter of the combined apparatus.

In an alternative embodiment shown in FIGS. 1A and 1B, the section 290 of the tip 280 is extremely long and tapered, and is sharp as a standard cannula or needle at its distal end, such that the tool 250 may be used for initial insertion of the catheter, without the need for an extra needle and guide wire. The tool 250 is still, in this embodiment, used for manipulating the mechanism 60.

When the locking mechanism 60 is in its fully extended position, it has an outer diameter which is substantially the same as the outer diameter of the catheter 10, such that the mechanism 60 provides minimal resistance to insertion of the catheter into the stomach. This avoids the necessity of creating a hole with a diameter larger than the gastrostomy catheter through the stomach wall to accommodate the locking mechanism. Also, the catheter 10, being of a flexible, somewhat elastic material, is slightly stretched as the insertion tool is used to place the catheter within the stomach. Since the catheter has a larger diameter than that of the needle 370, the catheter 10 or catheter 510 enlarges the opening originally made with the needle 370. This results in a very tight fit with the opening, which reduces or eliminates the problem of gastric leakage. The fit of the catheter is made even tighter by the fact that it is stretched thin while it is being inserted, such that it reexpands upon release of the tension on it, filling the opening snugly.

The guide wire is preferably long enough such that its proximal tip 420 extends out of the handle 270 when the insertion tool 250 and catheter 10 are in place. Thus, the guide wire 390 may be removed once the tool 250 and catheter 10 are positioned, simply by pulling on its proximal tip 420.

Once the catheter 10 is in place, the operator of the device pulls back on the insertion tool 250, which brings the locking mechanism 60 into the configuration shown in FIGS. 1 and 3. This is done by the operator holding his or her fingers against the skin, one on either side of the catheter 10, and lightly squeezing the catheter. The tool 250 is then pulled back, thus opening the mechanism 60 up while the fingers maintain the catheter in place.

Once the mechanism 60 is locked in its expanded configuration, the operator pulls outward on the catheter, to seat the mechanism 60 against the inner wall of the stomach. Then, the operator slides the locking ring 350 against the skin 450, such that the catheter 10 is maintained tightly in place by the locking mechanism 60 and the locking ring 320. Then, the insertion tool 250 is rotated counterclockwise, such that the grooves 300 align with the knobs 110, and the insertion tool 250 is then removed. At this point, the gastrostomy catheter 10 is fixed in place, and conventional medical apparatus may be attached to the proximal end 20 for enteral feeding, delivery of medications, or the like.

When the catheter 10 is emplaced as described above, the patient's skin 450 will contact the ridges 340 of the locking ring 320, and the inner surface 460 of the patient's stomach will be adjacent the locking mechanism 60, as shown in simplified fashion in FIG. 1. The ring 320 may be positioned for a tight fit by sliding it relative to the catheter 10. It is helpful to pull back on the catheter 10, thus stretching it slightly—due to opposing forces from the pulling force and the anchor (i.e. mechanism 60), respectively—and then sliding the button or locking ring 320 against the patient's skin. Tension on the catheter is then maintained between the ring 320 and the anchor 60, resulting in a firm clamping configuration against the stomach wall and the skin of the patient.

When the catheter 10 is to be removed, the insertion tool 250 is reinserted such that the knobs 110 are again slid into the grooves 300 and then into the portions 310, and the insertion tool 250 is pushed inwardly until the locking mechanism 60 takes on the fully extended position. The insertion tool is then removed, and the catheter 10 may then be withdrawn from the stomach.

It will be appreciated from the foregoing that the catheter constitutes a primary catheter, i.e. a catheter for initial insertion into the patient. It is customary, or may be necessary for health reasons, to replace the primary catheter after a period of time with a secondary catheter, which maintains access to the patient's stomach for continued treatment.

Such a secondary catheter incorporating the present invention is shown in FIG. 6, wherein the locking mechanism 60 is as described above, but an insertion tool 470 having a blunt end 480 is used rather than the insertion tool 250. The tool 470 need not be hollow, as with the tool 250.

The end 480 includes grooves 300 and portions 310, which coact with the knobs 110 (shown in FIG. 6) in the same fashion as described above relative to FIG. 1-3. The catheter 510 of this embodiment differs in several respects from the catheter 10, including that the locking mechanism includes a rounded or blunt distal end or tip 525. The tapered end 90 of the catheter 10 shown in FIG. 1 is unnecessary in this embodiment, because the opening has already been formed in the patient. It is for this reason that both the end 480 and the end 525 are rounded or blunt.

In the embodiment of FIG. 6, a retaining button 490 is provided, and includes a relatively rigid, exteriorly threaded shaft 500. The catheter 510 also includes a relatively rigid shaft 520 which is preferably formed in unitary fashion with the shaft 500. The shafts 500 and 520 are in fact a continuous, generally cylindrical tube of moderately hard rubber or soft plastic, and are provided with circumferential grooves 522, as shown in FIG. 8. The total length of the shafts 500 and 520 may be varied by varying the length of the overlap region 524, which is accomplished by either pushing the shaft 500 towards the shaft 520 to maximize the overlap 524, thus minimizing the total length of the shafts 500 and 520; or by pulling them apart, thus minimizing the overlap 524 and maximizing the total length. The shafts 500 and 520 are maintained in their relative positions by the moderate stiffness of the material from which they are formed and by the grooves 522, which provide friction against relative longitudinal movement.

In an alternative embodiment, the shafts 500 and 520 may be provided with threads, such that their total length (and overlap) is governed by the degree to which they are threaded together.

The button 490 in a preferred embodiment may be of substantially the same design as the button 320.

A one-way valve 530 is carried by a rigid T-stem 540, which itself is carried tightly within the button 490. The T-stem 540 may be provided with an annular flange 550, and the valve 530 includes a corresponding annular groove 560 for retention purposes. The valve 530 is preferably formed of a flexible rubber, plastic, or other material, such that fluids may pass from left to right from the point of view of FIG. 6, but not from right to left. The rigidity of the shaft T-stem 540 prevents accidental opening of the valve 530 due to pressure or squeezing of the catheter.

The T-stem 540 is removable, along with the valve 530, by pulling outwardly on the T-stem, which may be desired, for instance, for decompression of the peritoneal cavity.

The valve 530 is provided to compensate for the fact that the shaft 520 is made relatively short in this embodiment. In the embodiment of FIG. 1, the length of the catheter 10 between the proximal end 20 and the distal end 50 is relatively long, such that, if fluids travel up the shaft thereof, they are prevented from exiting the proximal end 20 by back-pressure or head within the catheter. When the shaft is relatively short, as in the embodiment of FIG. 6, the fluids may not develop the necessary back-pressure, and thus the valve 530 is provided to keep such fluids from exiting the patient via the catheter 510.

It will be appreciated that the design of the catheter 510 is such that a wide variety of sizes of catheters may be made, with variations both in diameter and length; and this is also true for the catheter 10. For instance, the identical structure of the valve 530 may be used in a larger-diameter catheter merely by enlarging the diameter of the valve itself.

In FIG. 1, the sliding locking ring 320 allows this longer proximal end of the catheter 10, whereas the nonsliding retaining button 490, shown in FIG. 6, causes the catheter 510 to be shorter because of the limiting factor of the distance of the button 490 from the locking mechanism 545. In an alternative embodiment (not separately shown), however, the catheter 510 may be provided with an additional proximal length to the left of button 490, to provide the pressure or head necessary to keep fluids from flowing out of the stomach through the catheter 510. In such a configuration, the valve 530 may be dispensed with.

Figure 10:
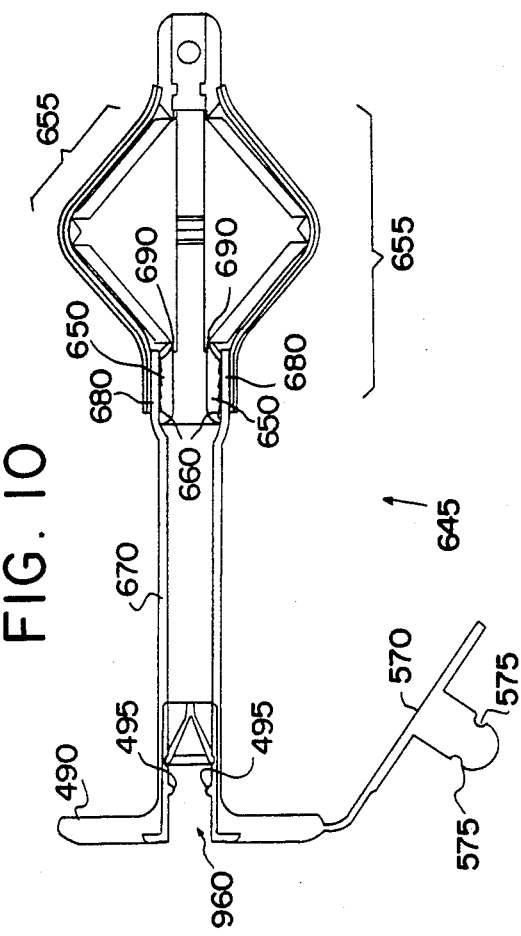
FIG. 10 shows another alternative embodiment to the apparatus of FIG. 6.

The button 490 is provided with a plug 570, which is attached in a hinged or otherwise flexible fashion to the main portion of the button 490, such as by means of a rubber flap 580. The plug 570 fits snugly into the bore 960, and is provided with an annular groove 495 for interacting with an annular groove 495 within the bore 960, as shown in FIG. 10.

The catheter 510 is used in conjunction with the insertion tool 470 in much the same manner as the device described relative to FIG. 1 above. However, because the catheter 510 is a secondary catheter, the opening for access to the patient's stomach, i.e. the track or stoma, is already formed when the catheter 510 is put to use.

In order to insert the catheter 510, the insertion tool 470 is first inserted through the bore 590 of the catheter 510, for which purpose the plug 570 must be pulled out of the end of the button 490. The valve 530 is removed by pulling the T-stem 540 out, and then the tool 470 is inserted so that the knobs 110 are positioned into the portions 310 via the grooves 300, as described relative to the first embodiment. The catheter 510 is then inserted through the opening into the patient's stomach, and the locking mechanism 545 is pulled into its locking configuration, shown in FIGS. 3 and 6. The insertion tool 470 is then removed, and the valve 530 is replaced along with the T-stem 540. Medications, nutrients or the like may then be provided through the catheter 510, and will exit through the lateral ports 120 and the terminal port 100.

The shafts 500 and 520 are preferably adjusted as described above such that the distance between the button 490 and the locking mechanism 60 is approximately the same distance as that between the outer layer of skin 450 and the inner wall of the stomach 460 (shown in FIG. 1), for a tight fit. As described below relative to FIGS. 8 and 9, this distance may be made adjustable so that a single design of catheter may accommodate a variety of different lengths. This is particularly important for gastrostomy applications, since it is desirable that the stomach is firmly pressed against the abdominal wall, so that the two heal together while the catheter is in place. Such healing is useful especially for long-term emplacement of feeding catheters; without it, stomach fluids may leak into the peritoneum, causing peritonitis and other complications. The necessary firmness of the pressure on the stomach and the abdominal wall is achieved in the present invention both by the adjustability of the apparatus and by the fact that the anchor of the invention is formed from a rigid material.

FIG. 8 shows an alternative embodiment to the gastrostomy catheter 510 shown in FIG. 6, incorporating a locking mechanism 615 which may be utilized either with the catheter 510 or the catheter 10. In the embodiment shown in FIGS. 8-9, the catheter 600 is identical to the catheter 510, except for the locking mechanism. Thus, like catheter 510, catheter 600 is a secondary catheter, for use after a primary catheter (such as catheter 10) has been removed.

In FIGS. 8-9 and the other alternative embodiments discussed herein, it will be understood that features with the same numbers are identical or substantially identical. Where there are differences between identically-numbered structures due to different embodiments being depicted, these are noted in the discussion.

In the catheter 600, the branches 150A-180A include locking detents 150C-180C. In each of FIGS. 8 and 9, only legs 160 and 170 are shown, but it will be understood that the other legs may include similar locking detents. Similarly, branches 150B-180B include locking detents 150D-180D, which are configured to interlock with the detents 150C-180C. For instance, as shown in FIG. 8, detent 160C clips into detent 160D, and detent 170C clips into detent 170D. In this manner, when the insertion tool 470 is interlocked with the locking knobs 110 as described above, and the physician pulls back on the tool 470, the detents 150C-180C interlock with the detents 150D-180D, thus locking the entire mechanism 615 in place.

As shown in FIG. 8, a single detent may be utilized, or, as in FIG. 9, multiple detents may be utilized on the legs 150-180. The use of multiple detents has the advantage of providing a tighter locking configuration, while the use of a single detent for each branch has the advantage of being easier to snap into and out of the locking configuration.

Figure 9A:
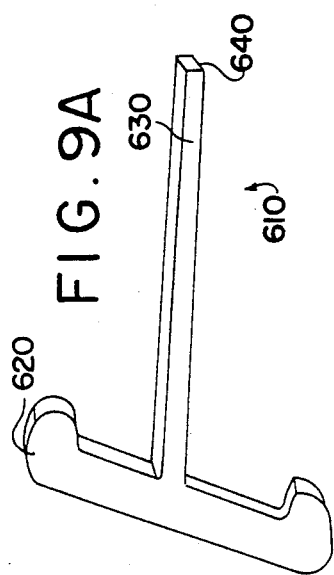
FIG. 9A shows a releasing tool for releasing the locking mechanism of the invention.

FIG. 9A shows a releasing tool 610 having a handle 620 and a shaft 630. In the preferred embodiment, the bore 15 of the catheter 10 (shown in FIG. 1) and the bore 515 of the catheter 510 (shown in FIG. 6) are rectangular in cross section, and closely match the shape of the shaft 630. However, the bore 100 (see FIG. 3) and the bore 535 of the tip 525 (see FIG. 6) are circular in cross section.

When the catheter 10, the catheter 510 or the catheter 600 is in the expanded configuration (as shown in FIGS. 1, 6, and 8-9 respectively), and the releasing tool 620 is inserted into the bore (15, 515 or bore 555 of mechanism 615) of the catheter such that the shaft 630 passes through the bore, a forward end 640 of the shaft 630 contacts the forward end 750 at a region just distal of the hinges 770, at which region the cross-section of the interior of the mechanism goes from a rectangular cross-section to a circular cross-section. The rectangular cross-section accommodates the tool 620 whereas the circular cross-section does not, so that pushing the tool 620 against the transition region forces branches 150B-180B away from branches 150A-180A. This returns the catheter to its non-locking position, such that it may be removed from the patient.

However, the tool 610 cannot be used to lock a mechanism (60, 545 or 615) in place, because the shaft 630 is configured such that it cannot engage the locking knobs 110 in such a manner as to pull back on the knobs. Thus, the tool 610 is a discriminatory tool, which can disengage but not engage the locking mechanisms of the respective catheters. This is a useful tool for medical technicians or nurses who are qualified to remove, but are not authorized to emplace, gastrostomy catheters.

A detailed view of an alternative embodiment of the catheter 510 shown in FIG. 6 appears in FIG. 10. In this embodiment, the locking mechanism 655 includes a collar 650 having external teeth 660. The catheter 645 of FIG. 10 includes a shaft 670 having a forward end 680 with internal teeth 690 which interlock with the teeth 660. Depending on how far the collar 650 is pushed into the shaft 670, the locking mechanism 655 may be moved closer to or farther from the retaining button 490, thus accommodating a variety of thicknesses of abdominal walls.

FIG. 14 shows an alternative embodiment of the primary cathether 10 FIG. 1, including a mechanism 840 similar to that of FIG. 10, surrounded by a membrane 850. The mechanism 840 in this embodiment includes a collar 860 with exterior teeth 870 which interlock with interior teeth 880 of a shaft 890. The mechanism 840 shown in FIG. 14 includes a tip 90 identical to the tip 90 shown in FIG. 1.

FIG. 15 shows the use of the catheter 645 shown in FIG. 10 in conjunction with a feeding adaptor 900, used for providing medicines, nutrients, or the like to the patient. FIG. 16 shows a top view of the configuration of FIG. 15, with the button 490 having ridges 910 for spacing the button 490 from the skin of the patient. The ridges 910 are shown in dotted fashion in FIG. 16, and are disposed on the underside of the button 490.

A coupling catheter port adaptor 920 is attached to the adaptor 900 by means of a connecting arm 930 having forwardly-angled ridges 940. The adaptor 900 is slightly elastic, and has an interior diameter which closely matches an exterior diameter of the exterior ridges 940. Thus, the adaptor 900 may be stretched slightly to fit over the ridges 940, and the forward angling of the ridges 940 keeps the catheter in place.

The coupling adaptor 920 includes a nipple 950 which fits tightly within the bore 960 of the button 490, and which includes an annular groove 925 which, like the groove 575 of the plug 570 (shown in FIG. 10), maintains the nipple 950 within the bore 960.

The adaptor 900 includes, at its proximal end 905, a med port 915 with a female luer connector for accommodating any standard male luer connector. The end 905 also has a catheter port 905, which fits conventional feeding bag connectors.

Thus, the adaptor 920, which may take on a variety of sizes and configurations, may be used to couple a variety of catheters 900 with different sizes of catheters 645. In the preferred embodiment, the arm 930 and the nipple 950 form a right angle, although other angles may be used.

Figure 23:
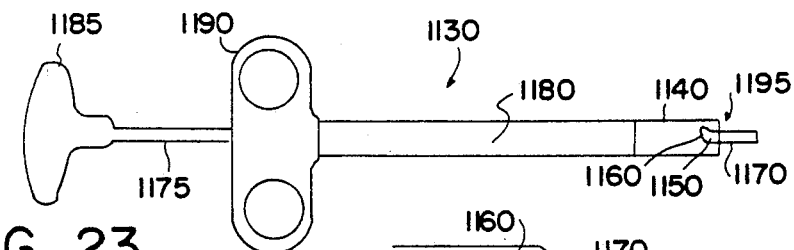
FIGS. 23-24 show an insertion tool for use with the embodiment of FIGS. 17-22.
Figure 24:
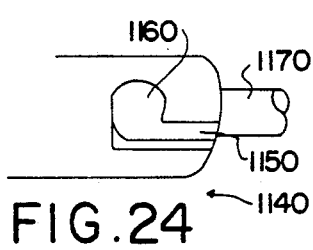

FIGS. 17-22 show an alternative embodiment of the invention, and FIGS. 23-24 show an applicator for use with the embodiment of the invention shown in FIGS. 17-21. In this embodiment, a locking mechanism 970 is provided, having legs 1010, 1020, 1030 and 1040. Note that only legs 1020 and 1030 are shown in FIGS. 17-20.

Each leg 1010-1040 includes a first branch and a second branch. Thus, referring to FIG. 21, leg 1010 includes a first branch 1010A and second branch 1010B; leg 1020 includes a first branch 1020A and a second branch 1020B; leg 1030 includes a first branch 1030A and a second branch 1030B; and leg 1040 includes a first branch 1040A and a second branch 1040B.

The mechanism 970 includes a tip 980 having internal ratchet teeth 990, as shown in FIGS. 17-20. Attached to the branches 1010A-1040A is a collar 1000 having exterior ratchet teeth 1050. The collar 1000 includes a locking knob 1070 in an interior bore 1080 thereof.

Figure 21:
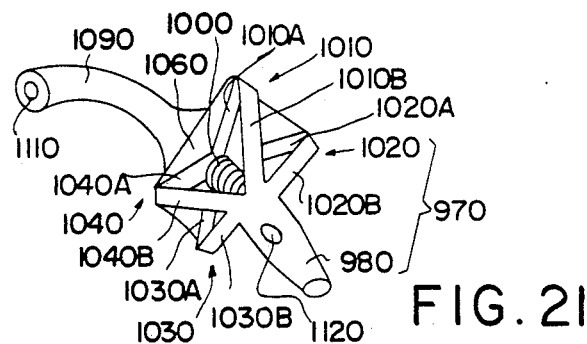
Figure 21:
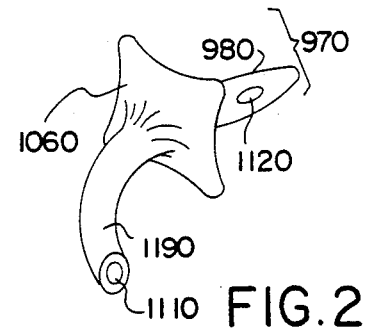

Carried in a sealed fashion rearwardly of the legs 1010-1040 is a membrane 1060, which is itself connected in a sealed fashion to a catheter 1090 as shown in FIG. 21. The tip 980 includes a bore 1100 which is in communication with the bore 1080, which in turn is in communication with a lumen 1110 of the catheter 1090. Ports 1120 may be provided in the tip 970.

Figure 17:
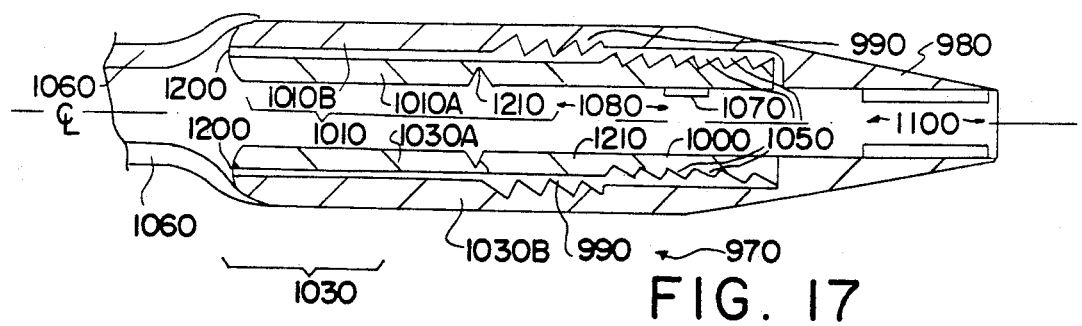

The initial configuration of the mechanism 970, ready for insertion into the patient, is shown in FIG. 17. The mechanism 970 is inserted into the opening into the stomach, as described above with respect to the earlier-discussed embodiments of the invention. This is accomplished by means of an insertion tool 1130 (shown in FIG. 23), which has a forward end 1140. The end 1140 includes a longitudinal groove 1150 which includes a portion 1160 at an angle (preferably a right angle) with respect to the longitudinal portion of the groove 1150.

The insertion tool has a shaft 1180 with an interior, longitudinal bore, in which a shaft 1175 having an end 1170 is slidably carried. Attached to the shaft 1175 is a handle 1185, and attached to the shaft 1180 is a handle 1190. A stop 1195 may be provided on the tip 1170 to prevent the shaft 1180 from slipping off the end of the shaft 1175; a complet stroke of the shaft 1180 relative to the shaft 1180 is then defined by the distance between the handles 1185 and 1190 when the end 1140 abuts the stop 1195.

In order to lock the mechanism 970 in place on the interior of the abdominal wall, the tip 1170 is inserted into the bore 1100. and is twisted until the groove 1150 engages the locking knob 1070. Once the mechanism 970 is pushed into the stomach, the tool 1130 may be twisted such that the locking knob 1070 is seated within the portion 1160. Then, the physician or operator of the mechanism retracts the forward end 1140 by pulling backwards on the handle 1190 (while holding the catheter so that the mechanism is not retracted), thus bringing the mechanism 970 into the position shown in FIGS. 18, 21 and 22.

Figure 18:
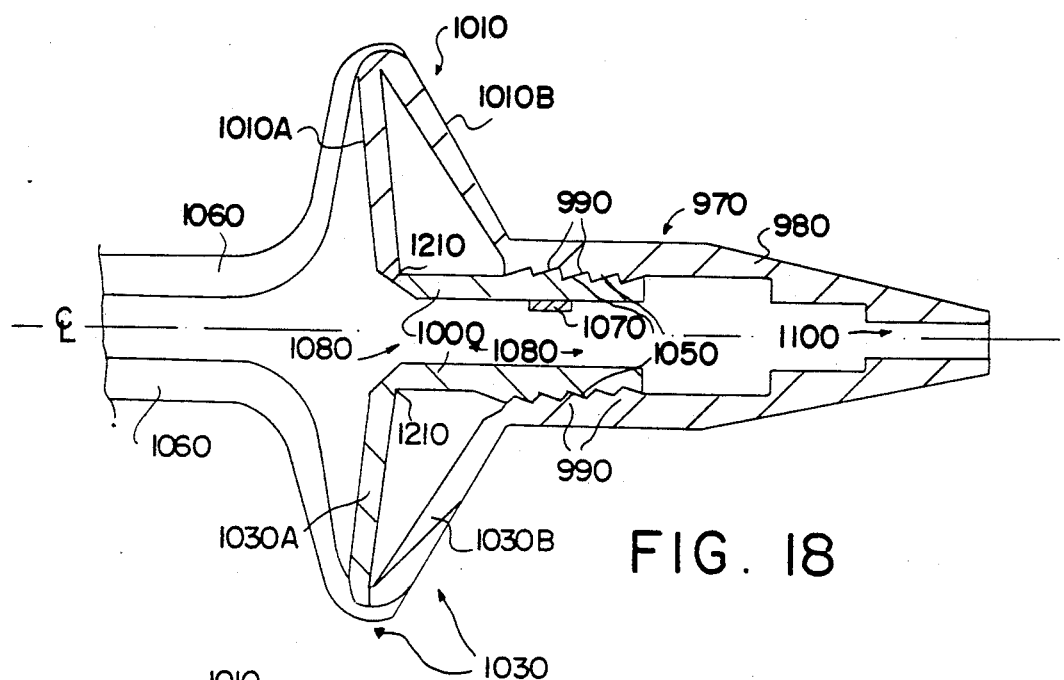

The relative lengths of the shaft 1175 and the shaft 1180 are such that one complete longitudinal movement of the handle 1190 from its forwardmost position relative to the handle 1185 to its rearmost position, or one complete stroke as defined above, corresponds in distance to the difference in the configurations of FIGS. 17 and 18, respectively. That is, when the handle 1190 (and hence the forward end 1170 and the collar 1000) moved back one complete stroke, the mechanism 970 goes from the collapsed configuration of FIG. 17 to the expanded configuration of FIG. 18.

Once the mechanism 970 is in place as in FIG. 18, the tool 1130 is then once again twisted such that the locking button is situated within the groove 1150, and the tool 1130 is then withdrawn. The catheter 1190 and mechanism 970 may be maintained in place by a retaining ring slid against the skin of the patient, as described above.

When the physician wishes to remove the mechanism 970, and thus remove the catheter 1090 from the patient, the forward end 1140 is again inserted into the bore 1080, and the locking knob 1070 is once again seated within the portion 1160. The user then pulls back on the handle 1190 in complete stroke, such that the mechanism 970 takes on the intermediate configuration shown in FIG. 19. Another complete stroke then collapses the mechanism 970 to a collinear configuration, as shown in FIG. 20. At this point, the mechanism 970 may be removed from the patient.

It will be appreciated that, because of the angling of the teeth 1050 and the teeth 990, the collar 1000 is prevented from moving forwardly with respect to the tip 980, once the teeth have engaged one another. Thus, when the mechanism 970 is in the configuration shown in FIG. 18, it is firmly locked in place, providing a reliable anchor for the catheter 1090. With the mechanism 970 in place within a patient, the force of the abdominal wall against the membrane 1060 and the branches 1010A-1040A works to keep the mechanism in place. Once this force is removed, however (such as if the mechanism is pushed further into the stomach so that the abdominal wall no longer contacts the membrane 1060), the collar 1000 is not prevented from moving rearwardly with respect to the tip 980; and thus, the mechanism 970 may be collapsed as shown in FIG. 20 and described above. Therefore, in removing the mechanism 970 as described above, it is preferable to first separate the membrane 1060 from contact with the patient.

Hinges 1200, 1210 and 1220 are provided (see FIGS. 19 and 20), and are configured such that the mechanism 970 may take on each of the configurations shown in FIGS. 17-20. Thus, hinges 1210 connect the collar 1100 with the branches 1010A-1040A, and are preferably thin membrane hinges dispose away from the bore 1080 (see FIG. 17) such that when collar 1000 is moved to the left from the point of view of FIG. 17, branches 1010A-1040A will be urged radially outward.

Likewise, hinges 1200 are preferably thin membrane hinges, as shown in FIG. 17 and 20, connecting branches 1010A-1040A to branches 1010B-1040B, respectively. Hinges 1200 are preferably disposed on the interior side of the respective branches, as shown in FIG. 20.

Figure 19:
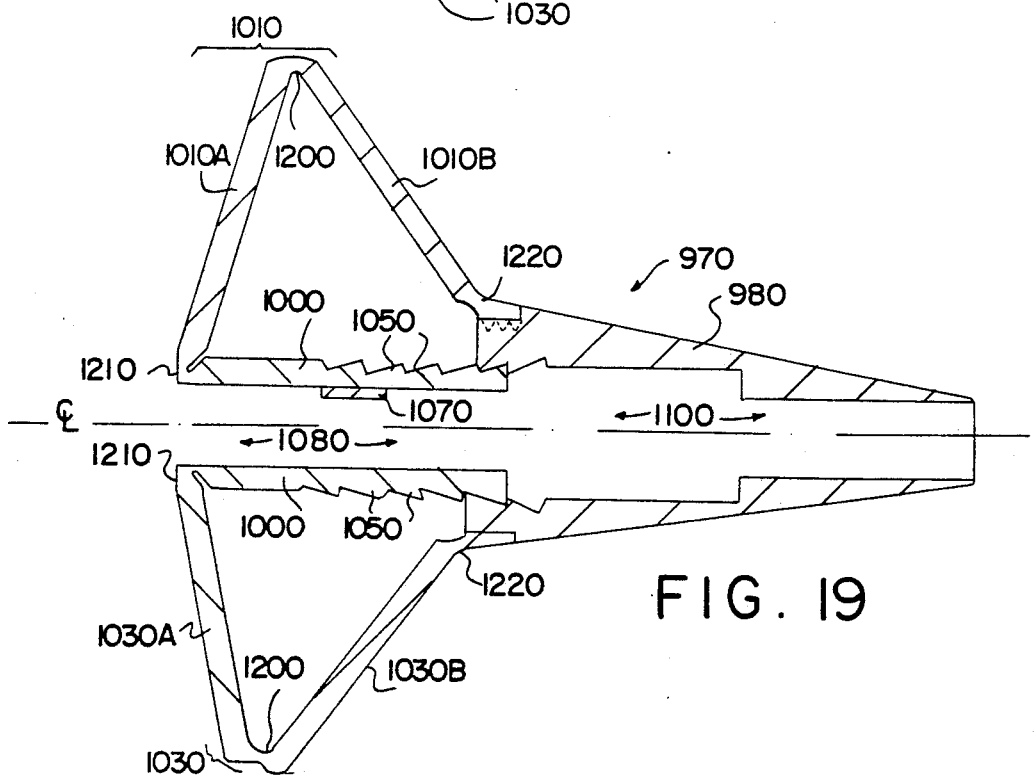
Figure 20:
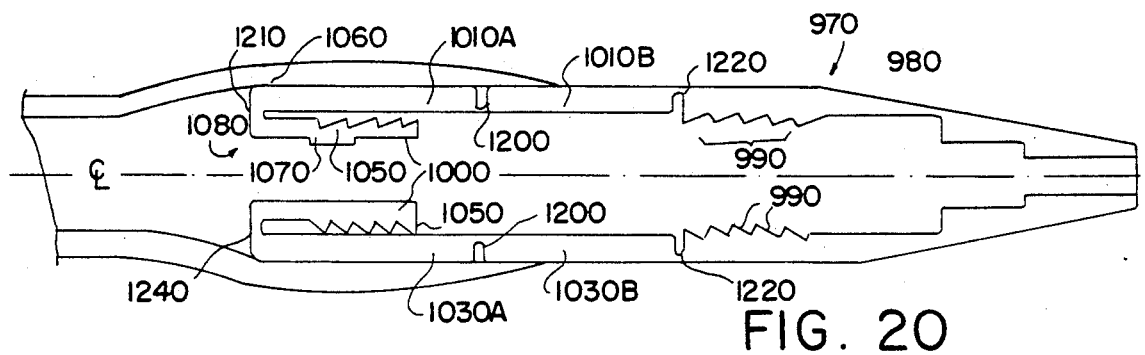

Similarly, hinges 1220 are preferably membrane hinges formed on the outside of their respective connections between the branches 1010B-1040B and the tip 980, as shown in FIGS. 19 and 20. This is to assist the legs 1010-1040 in being urged outwardly when the collar 1000 is pulled to the left from the point of view of FIGS. 17-20.

It will be appreciated that the method and apparatus of the invention, in their various embodiments, may be used not only in the form of primary and secondary gastrostomy catheters, but may be used in any application where it is desired to place a catheter or other such device into a patient, to provide fluids, allow for insertion of endoscopic or fiber optic apparatus, and other treatments. The present invention is especially useful where the pull procedure is not available, such as for use with certain organs or parts of the body where access can be had only from one direction.

Other variations and alternative embodiments may be made on the foregoing without departing from the spirit and scope of this invention.

What is claimed is:

1. An apparatus for providing access through an opening in a surface, comprising:
    an elongate tube having a proximal end, a distal end, and a main body, with an access passage through the tube;
    anchoring means attached to said distal end for anchoring said elongate tube at said opening, said anchoring means having a first configuration wherein an outer diameter of said anchoring means is substantially equal to an outer diameter of said tube, and having a second configuration wherein said anchoring means outer diameter is greater than said tube outer diameter;
    means for retaining said anchoring means in said second configuration, said retaining means including means for increasing resistance to repositioning to said first configuration when a radial force is applied to said anchoring means;
    means for manipulating said anchoring means into each of said first and second configurations, for insertion of said anchoring means and a portion of the tube through the opening while said anchoring means is in said first configuration, and for manipulating said anchoring means into said second configuration.

2. The apparatus of claim 1, wherein:
    said anchoring means includes a first end, a second end, and a middle portion, said middle portion including a plurality of legs, each leg having a first section and a second section, wherein each said first section is attached in a hinged fashion to said first end, and each said second section is attached in a hinged fashion to said second end, and each said first section is attached in a hinged fashion to at least one said second section, such that when said first and second ends are pulled away from one another, said anchoring means takes on said first configuration such that each said first section is substantially collinear with one said second section, and such that when said first and second ends are pushed towards one another, said anchoring means takes on said second configuration such that each said first section is substantially parallel and adjacent to at least one said second section.

3. The apparatus of claim 2, wherein said retaining means comprises an elastic membrane encasing said anchoring means in a tight-fitting fashion.

4. The apparatus of claim 2, wherein said first end includes a plurality of annular ridges for maintaining said anchoring means in a fixed, sealed relationship with said tube.

5. The apparatus of claim 2, wherein:
    said second end includes a bore in communication with said tube;
    said manipulating means includes an insertion tool and means disposed within said second end bore for coating with said insertion tool for pushing said anchoring means into said first configuration and for pulling said anchoring means into said second configuration.

6. The apparatus of claim 5, wherein said insertion tool includes an elongate, longitudinally rigid body including a tip having means for transmitting longitudinal force to said coacting means for moving said anchoring means into said second configuration.

7. The apparatus of claim 5, wherein said insertion tool includes an elongate, longitudinally rigid body including a tip having a first longitudinal portion and a second portion at one end thereof and at an angle to said longitudinal portion, said insertion tool being configured for insertion through said tube such that said longitudinal portion receives said coacting means, and such that said lateral portion receives said coacting means upon rotation of said insertion tool, for longitudinal locking together of said insertion tool and said anchoring means, such that longitudinal force on said insertion tool is transmitted to said second end of said anchoring means so as to move said second end relative to said first end for moving said anchoring means into said first and second configurations.

8. The apparatus of claim 1, wherein said retaining means comprises a ring, slidably attached to said tube.

9. The apparatus of claim 1, wherein said retaining means comprises a ring, fixedly attached to said tube.

10. The apparatus of claim 1, further comprising a one-way valve disposed within said tube.

11. The apparatus of claim 10, wherein said valve comprises a flexible, substantially cylindrical member having an opening which is normally closed, said opening being adapted for opening when pressure is applied from one direction and for closing when no pressure is applied. and when pressure is applied from another direction.

12. The apparatus of claim 10, wherein said one-way valve is removable.

13. An apparatus for providing access through an opening in a surface, comprising:
    an elongate tube having a proximal end, a distal end, and a main body, with an access passage through the tube;
    anchoring means attached to said distal end for anchoring said elongate tube at said opening, said anchoring means having a first configuration wherein an outer diameter of said anchoring means is substantially equal to an outer diameter of said tube, and having a second configuration wherein said anchoring means outer diameter is greater than said tube outer diameter;
    means for retaining said anchoring means in said second configuration;
    means for manipulating said anchoring means into each of said first and second configurations, for insertion of said anchoring means and a portion of the tube through the opening while said anchoring means is in said first configuration, and for manipulating said anchoring means into said second configuration;

wherein said anchoring means includes a first end, a second end, and a middle portion, said middle portion including a plurality of legs, each leg having a first section and a second section, and wherein each said first section is attached in a hinged fashion to said first end, and each said second section is attached in a hinged fashion to said second end, and each said first section is attached in a hinged fashion to at least one said second section, such that when said first and second ends are pulled away from one another, said anchoring means takes on said first configuration such that each said first section is substantially collinear with one said second section, and such that when said first and second ends are pushed towards one another, said anchoring means takes on said second configuration such that each said first section is substantially parallel and adjacent to at least one said second section;

and wherein each of said first sections has a first length and each of said second sections has a second length which is shorter than said first length.

14. An apparatus for providing access through an opening in a surface, comprising:

an elongate tube having a proximal end, a distal end, and a main body, with an access passage through the tube;

anchoring means attached to said distal end for anchoring said elongate tube at said opening, said anchoring means having a first configuration wherein an outer diameter of said anchoring means is substantially equal to an outer diameter of said tube, and having a second configuration wherein said anchoring means outer diameter is greater than said tube outer diameter;

means for retaining said anchoring means in said second configuration; and means for manipulating said anchoring means into each of said first and second configurations, for insertion of said anchoring means and a portion of the tube through the opening while said anchoring means is in said first configuration, and for manipulating said anchoring means into said second configuration;

wherein said anchoring means includes a first end, a second end, and a middle portion, said middle portion including a plurality of legs, each leg having a first section and a second section, wherein each said first section is attached in a hinged fashion to said first end, and each said second section is attached in a hinged fashion to said second end, and each said first section is attached in a hinged fashion to at least one said second section, such that when said first and second ends are pulled away from one another, said anchoring means takes on said first configuration such that each said first section is substantially collinear with one said second section, and such that when said first and second ends are pushed towards one another, said anchoring means takes on said second configuration such that each said first section is substantially parallel and adjacent to at least one said second section;

wherein each second end includes a bore in communication with said tube;

wherein said manipulating means includes an insertion tool and means disposed within said second end bore for coacting with said insertion tool for pushing said anchoring means into said first configuration and for pulling said anchoring means into said second configuration;

and wherein said insertion tool includes a bore for receiving a wire disposed in the opening in the surface.

15. A method for emplacement of a catheter into a patient, said catheter including a distal end having an expandable and collapsible anchor, including the steps of:

(1) interlocking an insertion tool with the anchor without applying longitudinal force to the anchor;

(2) passing the interlocked insertion tool and anchor into the patient such that the anchor enters the patient in its collapsed configuration;

(3) manipulating the insertion tool such that the anchor is expanded; and (4) removing the insertion tool without applying longitudinal force to the anchor, leaving the anchor within the patient.

16. The method of claim 15, further including, after step 4, the steps of:

(5) inserting a removal tool and again interlocking the anchor therewith;

(6) manipulating the anchor into its collapsed configuration; and (7) removing the removal tool and the anchor from the patient.

17. The method of claim 16, wherein the removal tool is the same tool as the insertion tool.

18. The method of claim 15, further including, before step 2, the step of:

(8) inserting a needle into the patient, thereby forming an opening;

wherein step (2) includes the step of passing the anchor through the opening.

19. The method of claim 18, wherein the anchor in its collapsed configuration has a diameter substantially the same as a diameter of the catheter, for preventing enlargement of the opening upon insertion of the catheter.

20. The method claim 18, including providing rigidity to the anchor for preventing accidental removal thereof from the opening.

21. A method of emplacement of a catheter into a patient, said catheter including a distal end having an expandable and collapsible anchor, including the steps of:

(1) inserting a needle into the patient, the needle having a lumen therethrough, thereby forming an opening;

(2) inserting a guide wire through the lumen of the needle;

(3) removing the needle;

(4) interlocking an insertion tool with the anchor;

(5) passing the interlocked insertion tool and anchor into the patient such that the anchor enters the patient in its collapsed configuration;

(6) manipulating the insertion tool such that the anchor is expanded; and (7) removing the insertion tool, leaving the anchor within the patient;

wherein the insertion tool is provided with a bore therethrough, and wherein step 5 includes the step of passing the bore over the guide wire for guiding it into the opening.

22. The method of claim 21 further including the step of providing the guide wire with a bight at its distal end, the bight being flexible for taking on a straightened configuration for passing through the lumen of the needle, but resuming the bight shape when no force is placed thereon, such that the guide wire is maintained within the opening in the patient by means of the bight after the needle is removed.

23. An anchor, comprising:
a first section;
a second section;
a middle section having a first end attached in a hinged fashion to said first section and a second end attached in a hinged fashion to said second section, said middle section having at least two configurations, namely an expanded configuration wherein the anchor has an enlarged diameter and a first collapsed configuration wherein the anchor has a reduced diameter;
means for grasping said second section and moving it in a first direction relative to said first section, such that said middle section takes on its expanded configuration, said grasping means also being for moving said second section in a second direction relative to said first section, such that said middle section takes on said first collapsed configuration; and
means, attached to said anchor, for maintaining said middle section in said expanded configuration, said maintaining means including means for increasing resistance to repositioning to said first collapsed configuration when a radial force is applied to said middle section.

24. The anchor of claim 23, wherein said middle section in said first collapsed configuration has a diameter substantially equal to a diameter of said first section, and in said expanded configuration has a diameter larger than said diameter of said first section.

25. The anchor of claim 24, wherein said middle section includes:
at least one first segment attached by a first hinge to said first section;
at least one said second segment attached by a second hinge to said second section; and
means for attaching said first segment in a hinged fashion to said second segment.

26. The anchor of claim 25, wherein said first and second segments are substantially collinear when said middle section is in said first collapsed configuration, and are substantially parallel when said middle section is in said expanded configuration.

27. The anchor of claim 25, wherein said maintaining means comprises means for preventing relative motion of said first and second segments.

28. The anchor of claim 25, wherein:
said first and second segments are configured for positioning at less than a right angle relative to an axis of said first section when said middle section is in said expanded configuration.

29. The anchor of claim 24, wherein said first and second segments are substantially parallel when said middle section is in said first collapsed configuration, and are at an angle to one another when said middle section is in said expanded configuration.

30. An anchor, comprising:
a first section;
a second section;
a middle section having a first end attached in a hinged fashion to said first section and a second end attached in a hinged fashion to said second section, wherein said middle section includes at least one first segment attached by a first hinge to said first section, at least one said second segment attached by a second hinge to said second section; and means for attaching said first segment in a hinged fashion to said second segment;
said middle section having at least two configurations, namely an expanded configuration of enlarged diameter and a first collapsed configuration of reduced diameter, wherein said middle section in said first collapsed configuration has a diameter substantially equal to a diameter of said first section, and in said expanded configuration has a diameter larger than said diameter of said first section;
means for grasping said second section and moving it in a first direction relative to said first section, such that said middle section takes on its expanded configuration, said grasping means also being for moving said second section in a second direction relative to said first section, such that said middle section takes on said first collapsed configuration; and
means for maintaining said middle section in said expanded configuration, wherein said maintaining means comprises means for preventing relative motion of said first and second segments, wherein said preventing means includes an elastic membrane positioned over said middle section and attached to at least one of said first and second sections, said membrane being in a stretched state when said middle section is in said expanded configuration, for exerting an axially inward force on said middle section.

31. The anchor of claim 30, wherein said attaching means comprises a stop attached by third hinge to said first segment and by a fourth hinge to said second segment, said stop having a first surface for abutting an end of said first segment and having a second surface for abutting an end of said second segment when said middle section is in said expanded configuration, for preventing relative motion of said first and second segments.

32. The anchor of claim 31, wherein:
said middle section defines an interior and an exterior of said anchor;
said first and second hinges are positioned adjacent said interior; and
said third and fourth hinges are positioned adjacent said exterior, such that when said second section is moved in said first direction, said first and second segments of said middle section are urged towards said exterior.

33. The anchor of claim 30, wherein:
said first section includes a first surface at an end thereof;
said first segment of said middle section includes a second surface at an end thereof;
said second segment of said middle section includes a third surface at an end thereof; and
said second section includes a fourth surface at an end thereof;
wherein said first, second, third and fourth surfaces are configured such that, when said middle section is in said expanded configuration, said first surface abuts said second surface and said third surface abuts said fourth surface, said first segment lies at a first predetermined angle relative to said first section, and said second segment lies at a second predetermined angle relative to said second section.

34. The anchor of claim 33, wherein said first predetermined angle is greater than ninety degrees, and said second predetermined angle is less than ninety degrees.

35. The anchor of claim 33, wherein said first predetermined angle is approximately 98 degrees, and said second predetermined angle is approximately 82 degrees.

36. The anchor of claim 33, wherein each of said first and second predetermined angles is selected such that said force is at a nonzero angle relative to at least one of said first and second segments of said middle section.

37. An anchor, comprising:
a first section;
a second section;
a middle section having a first end attached in a hinged fashion to said first section and a second end attached in a hinged fashion to said second section, wherein said middle section includes at least one first segment attached by a first hinge to said first section, at least one said second segment attached by a second hinge to said second section; and means for attaching said first segment in a hinged fashion to said second segment;
said middle section having at least two configurations, namely an expanded configuration of enlarged diameter and a first collapsed configuration of reduced diameter, wherein said middle section in said first collapsed configuration has a diameter substantially equal to a diameter of said first section, and in said expanded configuration has a diameter larger than said diameter of said first section;
means for grasping said second section and moving it in a first direction relative to said first section, such that said middle section takes on its expanded configuration, said grasping means also being for moving said second section in a second direction relative to said first section, such that said middle section takes on said first collapsed configuration; and
means for maintaining said middle section in said expanded configuration, wherein said maintaining means comprises means for preventing relative motion of said first and second segments, wherein said preventing means includes means for interlocking said first and second segments to one another when said middle section is in said expanded configuration.

38. The anchor of claim 37, wherein said interlocking means includes complementary detents formed on each of said first and second segments.

39. The anchor of claim 38, wherein said interlocking means includes:
first teeth disposed on said first section and angled in a third direction; and
second teeth disposed on said second section and angled in a fourth direction;
wherein said first and second teeth engage one another when said middle section is in said expanded configuration, for preventing relative motion of said first and second sections, thereby also preventing relative motion of said first and second segments.

40. The anchor of claim 39, wherein said first, second and fourth directions are the same, and said third direction is opposite to said fourth direction.

41. The anchor of claim 39, wherein:
said middle section has a second collapsed configuration; and
said first hinge is configured for allowing said first segment to lie adjacent and parallel to said first section when said middle section is in said first collapsed configuration, and is configured also for allowing said first segment to lie at an angle relative to said first section when said middle segment is in said expanded configuration, and is further configured for allowing said first segment to lie collinear with said first section when said middle section is in said second collapsed configuration.

42. The anchor of claim 41, wherein said angle is less than ninety degrees.

43. The anchor of claim 41, wherein said first hinge is configured for accommodating at least 180 degrees of relative positions of said first segment and said first section.

44. The anchor of claim 39, wherein said first teeth are positioned on a first side of said second teeth when said middle section is in said first collapsed configuration, are positioned adjacent said second teeth when said middle section is in said expanded configuration, and are positioned on a second side of said second teeth when said middle section is in said second collapsed configuration.

45. An anchor, comprising:
a first section;
a second section;
a middle section having a first end attached in a hinged fashion to said first section and a second end attached in a hinged fashion to said second section, wherein said middle section includes at least one first segment attached by a first hinge to said first section, at least one said second segment attached by a second hinge to said second section; and means for attaching said first segment in a hinged fashion to said second segment;
said middle section having at least two configurations, namely an expanded configuration of enlarged diameter and a first collapsed configuration of reduced diameter, wherein said middle section in said first collapsed configuration has a diameter substantially equal to a diameter of said first section, and in said expanded configuration has a diameter larger than said diameter of said first section;
means for grasping said second section and moving it in a first direction relative to said first section, such that said middle section takes on its expanded configuration, said grasping means also being for moving said second section in a second direction relative to said first section, such that said middle section takes on said first collapsed configuration; and
means for maintaining said middle section in said expanded configuration, wherein said maintaining means comprises means for preventing relative motion of said first and second segments, wherein said preventing means includes means for interlocking said first and second sections to one another when said middle section is in said expanded configuration.

46. An apparatus for inserting a tube through an opening, the tube including a proximal end and a distal end, including:
anchoring means attached to said distal end of the tube for anchoring the tube at said opening, said anchoring means having a first resting configuration wherein an outer diameter of said anchoring means is no greater than approximately a diameter of said tube, and having a second resting configuration wherein said outer diameter of said anchoring means is greater than said diameter of said tube;

means for manipulating said anchoring means into each of said first and second configurations, for insertion of said anchoring means through the opening while said anchoring means is in said first configuration, and for maintaining the tube in place relative to the opening while said anchoring means is in said second configuration; and means, attached to said anchoring means, for maintaining said anchoring means in said second resting configuration, said maintaining means including means for increasing resistance to repositioning to said first resting configuration when a radial force is applied to said anchoring means.

47. The apparatus of claim 46, wherein:
said tube includes a lumen;
said anchoring means includes a bore in communication with said lumen of said tube; and
wherein said manipulating means is for manipulating said anchoring means between said a first configuration of enlarged diameter and a second configuration of reduced diameter from within said bore, said manipulating means passing through said lumen of said tube.

48. A method of emplacement of a tube into an opening, the tube including a lumen and a distal end and an anchor attached to the distal end, where the anchor has a bore in communication with the lumen, including the steps of:

(1) interlocking an insertion tool with the anchor without applying longitudinal force to the anchor;

(2) passing the anchor through the opening by means of the insertion tool, with the anchor in a first configuration wherein an outer diameter of the anchor is no greater than approximately an outer diameter of the tube;

(3) manipulating the anchor from within the bore, by means of the insertion tool, such that the anchor is moved into an expanded configuration wherein the outer diameter of the anchor is greater than the outer diameter of the tube, such that the tube seats within the opening with the anchor on one side of the opening; and (4) unlocking the insertion tool from the anchor, without applying longitudinal force to the anchor, and removing the insertion tool.

49. The method of claim 48, wherein step 2 is accomplished by a rigid insertion tool.

50. The method of claim 48, including the step of enlarging the opening by passing the tube therethrough, wherein a diameter of the enlarged opening is substantially equal to an outer diameter of the tube.

* * * * *